(12) United States Patent
Russo et al.

(10) Patent No.: US 11,298,466 B2
(45) Date of Patent: Apr. 12, 2022

(54) NEEDLE CAPTURE RETRACTABLE NEEDLE SAFETY SYRINGES

(71) Applicant: UNL Holdings LLC, New York, NY (US)

(72) Inventors: Robert Scott Russo, Malvern, PA (US); Brandon J McKee, Nesquehoning, PA (US); John W Carosi, Collegeville, PA (US); Jyoti Gupta, Atlanta, GA (US)

(73) Assignee: UNL HOLDINGS LLC, New York, NY (US)

( * ) Notice: Subject to any disclaimer, the term of this patent is extended or adjusted under 35 U.S.C. 154(b) by 184 days.

(21) Appl. No.: 14/777,713

(22) PCT Filed: Mar. 27, 2014

(86) PCT No.: PCT/US2014/032014
§ 371 (c)(1),
(2) Date: Sep. 16, 2015

(87) PCT Pub. No.: WO2014/160864
PCT Pub. Date: Oct. 2, 2014

(65) Prior Publication Data
US 2016/0279344 A1 Sep. 29, 2016

Related U.S. Application Data

(60) Provisional application No. 61/806,219, filed on Mar. 28, 2013.

(51) Int. Cl.
*A61M 5/32* (2006.01)
*A61M 5/50* (2006.01)

(52) U.S. Cl.
CPC .......... *A61M 5/3221* (2013.01); *A61M 5/322* (2013.01); *A61M 5/3234* (2013.01);
(Continued)

(58) Field of Classification Search
CPC .... A61M 5/322; A61M 5/3221; A61M 5/329; A61M 5/508; A61M 2005/323;
(Continued)

(56) References Cited

U.S. PATENT DOCUMENTS 4,747,829 A * 5/1988 Jacob ..................... A61M 5/322
604/110
4,995,870 A * 2/1991 Baskas ................... A61C 19/00
604/110

(Continued)

FOREIGN PATENT DOCUMENTS

EP 0340899 A2 11/1989
EP 0442260 A1 * 8/1991 .......... A61M 5/5066
(Continued)

OTHER PUBLICATIONS

"Barb." Merriam-Webster.com Dictionary, Merriam-Webster, https://www.merriam-webster.com/dictionary/barb. Accessed May 5, 2020. (Year: 2020).*
(Continued)

*Primary Examiner* — Rebecca E Eisenberg
*Assistant Examiner* — Tania Ismail
(74) *Attorney, Agent, or Firm* — Hamilton, Brook, Smith & Reynolds, P.C.

(57) ABSTRACT

Needle assemblies for retractable needle syringes include a needle, a needle seal, and a needle retainer, wherein the needle includes one or more barbs substantially at its proximal end. The needle retainer engages an optional needle-over-mold component that is fixedly attached to the needle. The needle-over-mold may be connected to the distal surface of the needle seal and may travel, such as by being a couple component, with the needle during the operation of the syringe. A safety syringe includes a barrel having a needle assembly mounted at a distal end and a plunger
(Continued)

assembly mounted at a proximal end. A drug may be contained in a drug chamber of barrel, between the plunger assembly and needle assembly, proximally of the needle seal for drug delivery to a user. The plunger assembly includes a plunger seal having a needle-engaging portion to capture the needle at the barb for retraction.

13 Claims, 19 Drawing Sheets

(52) U.S. Cl.
CPC ....... *A61M 5/508* (2013.01); *A61M 2005/323* (2013.01); *A61M 2005/3231* (2013.01); *A61M 2005/3235* (2013.01); *A61M 2207/00* (2013.01)

(58) Field of Classification Search
CPC .. A61M 2005/3231; A61M 2005/3235; A61M 2005/3228; A61M 5/3234
See application file for complete search history.

(56) References Cited

U.S. PATENT DOCUMENTS

| | | | | |
|---|---|---|---|---|
| 5,047,016 A | * | 9/1991 | Dolgin | A61M 5/3243 604/110 |
| 5,180,370 A | * | 1/1993 | Gillespie | A61M 5/3202 604/110 |
| 5,221,262 A | * | 6/1993 | Kite | A61M 5/3232 604/110 |
| 5,374,250 A | * | 12/1994 | Dixon | A61M 5/322 600/576 |
| 5,382,235 A | * | 1/1995 | Sak | A61M 5/322 604/110 |
| 5,415,648 A | * | 5/1995 | Malay | A61M 5/322 604/110 |
| 10,092,708 B2 | * | 10/2018 | Thorley | B32B 37/142 |
| 2005/0033228 A1 | | 2/2005 | Wang | |

FOREIGN PATENT DOCUMENTS

| | | |
|---|---|---|
| JP | 9-501078 A | 2/1997 |
| JP | 2003-516194 A | 5/2003 |
| WO | WO 89/09075 A1 | 10/1989 |
| WO | WO 92/19299 A1 | 11/1992 |
| WO | WO 98/51358 A1 | 11/1998 |
| WO | WO 2004/091699 A1 | 10/2004 |

OTHER PUBLICATIONS

International Search Report and Written Opinion from International PCT Application No. PCT/US2014/032014 (dated Aug. 19, 2014).

* cited by examiner

NEEDLE CAPTURE RETRACTABLE NEEDLE SAFETY SYRINGES

CROSS-REFERENCE TO RELATED APPLICATIONS

This patent application is a national phase of P.C.T. Application No. PCT/US2014/032014, filed Mar. 27, 2014, which claims the benefit of U.S. Provisional Application No. 61/806,219, filed Mar. 28, 2013, both of which are incorporated by reference.

FIELD

The present invention relates to safety syringes. More specifically, the embodiments of the present invention relate to needle capture retraction safety mechanisms, syringes which integrate such safety mechanisms, methods for manufacturing such safety syringes, and their methods of use.

BACKGROUND

Manually activated pre-filled syringe cartridges are commercially available from a variety of manufacturers, including the owner and assignee of the present invention. Pre-filled syringe cartridges are used in the administration of drug solutions, drug suspensions, vaccines, medicinal therapies, and any other liquid medicament by parenteral injection.

As such, pre-filled syringe cartridges include a primary drug chamber, a hypodermic needle permanently affixed to and in fluid communication with the drug chamber, and a piston slidably received in the drug chamber. The pistons of the pre-filled syringe cartridges often include a plunger sub-assembly, which may include a plunger inner and a plunger outer, to force the liquid medicament from the needle. Pre-filled syringes are typically prepared by pharmaceutical companies or sterile filling contractors in a sterile filling room in which the drug and the syringe are brought together in a sterile manufacturing environment wherein all components and drug solutions are isolated from microbial contamination.

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

Furthermore, health professionals may be exposed to used syringes, which can lead to inadvertent needlestick injuries and possible exposure to infective pathogens or other contaminants. In response to this problem, retractable syringes have been developed with the aim of preventing syringe re-use and/or needlestick injury by used syringes.

In developing such retractable syringes, relatively complicated retractable needle assemblies have been devised which often are developed for a particular syringe barrel shape or configuration and cannot be readily mounted to a syringe barrel having a different shape or configuration. This is particularly a problem with glass syringe barrels, which are generally in short supply, many of which glass barrels do not have a desired shape or configuration for mounting a retractable needle assembly. Accordingly, many existing safety syringes require specifically-tailored retraction mechanisms and barrel configurations, which may require complex manufacturing processes or operational changes. The materials employed in the manufacture of such safety syringes must meet complex criteria for regulatory approval. Additionally, safety syringes must remain aesthetically-similar to conventional syringes to facilitate broad adoption and must be easy-to-use for self-administering patients.

SUMMARY

Embodiments of the present invention relate to barrel-adaptable needle retraction systems and needle assemblies, syringes which integrate such safety mechanisms, methods of manufacturing such safety syringes, and their methods of use. Embodiments of the present invention provide reliable needle retraction, for improved user safety, without requiring complex manufacturing processes or operational changes for pharmaceutical companies or contract drug fillers. Additionally, embodiments of the present invention provide configurations which utilize materials and components which are readily employable for pharmaceutical use, many of which are increasingly considered off-the-shelf or standard components. Furthermore, the present invention provides components and devices which are aesthetically-similar to conventional syringes, which do not have needle retraction mechanisms, are ergonomically attractive to end-users, such as a medical practitioners and self-administering patients, and provide highly desired integrated safety features. The novel needle assemblies of the present invention are notably able to be adapted to primary drug barrels of varying configurations and materials such as, preferably, straight-barrel glass barrels to provide integrated needle assemblies and retraction mechanisms to the barrel. Such embodiments may be utilized for pre-filled or fill at time-of-use injectable drug syringes. As such, the adaptable retraction mechanisms of the present invention may be flexibly attached, affixed, mounted, or otherwise mated to standard barrels, such as straight-glass barrels. These embodiments, accordingly, provide novel and cost-efficient components and devices which are readily integrated into drug filling processes.

In an aspect of the invention, there is provided a retractable needle comprising a cannula that comprises a delivery tip comprising one or more inlet apertures and a proximal end comprising one or more apertures in fluid communication with the one or more delivery apertures in the delivery tip, the retractable needle further comprising one or more projections engageable by a plunger, wherein said one or more inlet apertures of the proximal end of the cannula are located distally of the one or more projections. The retractable needle is suitably disposed at least partially within the distal end of a syringe barrel, and adapted to move or retract from an insertion position in which the needle extends from a distal end of the barrel to a retracted position in which the needle is disposed within the barrel. The retractable needle may further comprise a body, the one or more projections located on the body. Preferably, the one or more projections are located on the cannula, preferably at the proximal end. The one or more projections may comprise one or more barbs that are engageable by the plunger, or by a plunger seal mounted to the plunger. Suitably, the proximal end of the cannula is capable of puncturing the plunger seal so that the one or more barbs are subsequently engaged within an internal chamber in the plunger seal. A retractable plunger assembly may be utilized to incorporate a retraction mechanism into the safety syringe, for retraction of the needle after it has been captured by the plunger seal of a plunger assembly. In certain embodiments, the retractable needle may comprise a needle-over-mold (NOM) that houses at least part of the cannula. Suitably, the cannula extends from the NOM so that at least the delivery tip is exposed.

In another aspect of the invention, there is provided a needle assembly for a syringe having a barrel and a plunger, the needle assembly comprising the retractable needle of the first aspect, a retainer and a needle seal. The needle retainer may be adapted to be engaged with a distal end of the barrel. The needle retainer may be adapted to be sealingly engaged with a distal end of the barrel.

In a further aspect of the invention, there is provided a retractable syringe including a barrel, a plunger assembly adapted to move within the barrel, and a needle assembly mounted to the barrel. Suitably, the needle retainer of the needle assembly is sealingly engaged with a distal end of the barrel. A flange may be included in at least one embodiment of the syringe to, for example to close off the proximal end of the syringe and barrel from the outside environment and/or to provide a tangible aspect for ergonomic gripping of the syringe.

Suitably, the plunger comprising a plunger seal that is puncturable or otherwise penetrable by the proximal end of the retractable needle. The plunger seal suitably comprises a needle-engaging portion that can engage the one or more projections of the retractable needle to thereby facilitate retraction of the retractable needle. A retraction mechanism of the plunger assembly is configured to maintain the biasing member in an energized position when the plunger assembly is not activated and release the biasing member when actuated. The retraction mechanism is actuable by depression of the plunger assembly, the biasing member being disposed to move the needle from the insertion position to the retracted position when the biasing member is released from the energized position. In one embodiment, the plunger may further comprise a plunger outer, a plunger rod and a biasing member, wherein the plunger outer and plunger rod so-operate to maintain the biasing member in an initially energized state. Disengagement of the plunger outer and the plunger rod facilitate release of the biasing member to thereby retract the retractable needle when engaged with the plunger or plunger seal.

In yet another aspect of the invention there is provided a method of assembling a retractable syringe that includes the steps of: (i) disposing a plunger assembly to move within a barrel of the retractable syringe; and (ii) mounting the needle assembly of the aforementioned aspect to the barrel. In some embodiments, the method may include fixedly engaging a needle retainer of the needle assembly aspect in the barrel. Suitably, the method includes disposing the needle assembly in a barrel tip for movement of the retractable needle between an insertion position wherein a needle of the needle assembly extends from the barrel tip and a retracted position wherein the needle is disposed within the barrel. Suitably, the plunger comprises at least part of a needle retraction mechanism including a biasing member.

Accordingly, in an embodiment the present invention provides a method for assembling a safety syringe having a needle assembly, a plunger assembly, and a barrel having a longitudinal axis. One method for assembling a safety syringe having a needle assembly, a plunger assembly, and a barrel having a longitudinal axis includes the steps of: assembling the needle assembly; mounting the needle retainer of the needle assembly to a distal end of the barrel; and mounting the plunger assembly to a proximal end of the barrel. The needle assembly may be fixedly mounted, such as by glue, to the distal end of the barrel. The plunger assembly may be movably mounted to the distal end of the barrel by first inserting the plunger seal into the barrel and then inserting the plunger rod into the plunger seal by screw connection or another known method of connection. The method for assembling the safety syringe may further include the step of filling the barrel with a drug, after the step of mounting the needle retainer of the needle assembly but prior to the step of mounting the plunger assembly.

In a still further aspect, the present invention relates to a method of use for a retractable syringe comprising a needle assembly according to the aforementioned aspect, a plunger assembly and a barrel, said method including depressing the plunger assembly to facilitate delivery of a substance from the barrel; and triggering a retraction mechanism to facilitate retraction of the needle. Suitably the barrel has a longitudinal axis. The method of use may includes the steps: depressing the plunger assembly to facilitate delivery of a drug from the barrel; upon completion of the drug delivery, triggering the retraction mechanism to release the biasing member from its energized state; and, by contact between the needle engaging portion of plunger seal and the needle barb of needle, causing the needle and/or the needle assembly to retract into the barrel. Regardless of the particular components, the methods of use for the safety syringes of the present invention are relatively similar. By capturing the needle prior to or simultaneously with activation of the retraction mechanism of the plunger assembly, the biasing member is allowed to expand causing the needle assembly and/or needle to retract in the proximal direction substantially along a longitudinal axis of the barrel. In some embodiments of the present invention, the entire needle assembly is caused to retract, while in other embodiments only certain components thereof, including the needle, are caused to retract upon expansion of the biasing member. Optionally, the method of use may include the step of blocking, with a clip or lock, the needle from axially translating in the distal direction after the needle has retracted into the barrel.

Accordingly, the aforementioned needle assembly includes components necessary for needle retention and retraction, and are configured to mate with standard barrels. The needle assembly is configured to mate and be affixed, through a number of known methods, to the distal end of a barrel. In at least one embodiment, the needle assemblies are configured to mate with barrels that are substantially straight in cross-sectional profile (e.g., substantially parallel along at least a distal portion of the barrel), such as glass straight-barrels. The needle assemblies may be configured to mate with the barrel in a number of different ways. In a preferred embodiment, however, the needle assemblies are configured such that at least a proximal connecting portion is shaped to be mounted to and reside within the inner diameter of a distal portion of the barrel. As such, the needle assembly may be connected to a standard straight-barrel drug chamber by being inserted into and attached, affixed, mounted, or otherwise mated to the distal end of the barrel. This enables the needle assemblies to be flexibly adaptable to barrels of all types, particularly standard glass straight-barrels, thereby providing potential manufacturing advantages and operational cost-savings. The needle assemblies of the present invention, therefore, simplify the assembly of needle retraction mechanisms with standard barrels to produce syringes with integrated needle safety features. In any of these embodiments of the needle assembly, the biasing member is mounted, either fixedly or movably, generally within the barrel tip. The biasing member is biased to expand in the proximal direction and substantially along the longitudinal axis of the barrel.

The needle assembly of the present invention enables selection and adaptation of varying needle assemblies with standard barrels. In other words, the design and configuration of the present invention allows a user to select a needle and/or needle assembly of a particular design or dimensions and adapt it to a syringe barrel for drug delivery. Accordingly, the needle assemblies of the present invention enable further customization of the drug delivery device by the user, allowing them to employ the integrated retraction mechanism of the needle assembly to any barrel to produce a safety syringe. For example, the needle and needle assemblies may be configured to provide a number of different needle lengths. The user may then select the needle assembly with their desired needle length and adapt it to a syringe to deliver the drug. This flexibility of the present invention is particularly useful for drug delivery that is subcutaneous or intramuscular. The needle assemblies of the present invention may be configured to enable such flexibility. One or more additional components may be utilized to provide this adaptive feature. For example, one or more connecting components may be utilized to connect the barrel tip of the needle assembly to the barrel. In one such embodiment, one connecting component (such as a receiving component) may be fixedly mounted on a distal end of a glass barrel. The receiving component may directly receive and engage the barrel tip with the integrated retraction mechanism. Alternatively, the needle assembly may include one or more additional connecting components (such as a mating component) which are used to engage the receiving component. Other optional components, such as elastomeric seals, which are known to one having ordinary skill in the art, may be necessary and incorporated into the device to facilitate the connection between the needle assembly and the barrel.

Additionally, the needle assemblies of the present invention utilize materials that are substantially non-reactive with therapeutic fluids or drugs, and are suitable for use in pharmaceutical grade applications. The novel needle assemblies are configured to minimize or eliminate the possibility of contact or interaction between degradable materials, such as certain plastics, with the therapeutic fluids or drugs. The needle assemblies, with adaptable needle retention and retraction mechanisms, also provide fluid pathways from the primary drug chamber to the patient, through the needle, which are substantially absent of degradable materials. Such novel adapter configurations, when integrated into barrels to provide the novel safety syringes of the present invention, provide increased stability and shelf-life parameters to the drug and drug delivery devices. These characteristics are thought to be highly desirable for generally all pharmaceutical treatments, but may be of particular advantage in syringes for use with biologics and other complex therapies. In one embodiment, for example, a metal needle is retained within a glass barrel by an elastomeric needle seal at a proximal end of the needle and by an aperture of a plastic barrel tip at a portion of the needle that is distal to the needle seal, such that the drug fluid pathway contains (and the drug contacts) only glass, elastomer, and metal. In this way, the drug travels from drug chamber to patient without contacting any plastic. In other embodiments, other material combinations or fewer materials may be utilized for the drug fluid pathway. Embodiments of the present invention also substantially reduce the number of components necessary for integrated needle retention and retraction mechanisms. Elimination of such components can further reduce the possibility of drug interaction with degradable materials, while also providing potential manufacturing advantages and operational cost-savings. The reduction of components in some embodiments of the present invention can be achieved by utilizing certain components for multiple functions.

One or more embodiments of the present invention may optionally include certain standard components. For example, the needle assembly configurations and syringe devices of the present invention may include one or more O-rings. In at least one embodiment, one or more O-rings are employed to seal the barrel tip within the barrel and/or to ensure a sterile environment and container integrity within the drug chamber of the barrel. Additionally or alternatively, the needle assembly may include one or more controlling members to facilitate the control of the rate of retraction. Similarly, the needle assembly may include one or more needle blocks, such as clips, flaps, flanges, or the like, which function to prevent the needle from being translated or protruding out of the barrel through the aperture of the barrel tip after the retraction mechanism has been initiated or completed. Furthermore, the safety syringe may include one or more components for aesthetics, ease-of-use, or other purposes. For example, one or more embodiments of the present invention may include a finger flange.

The novel needle assembly designs of the present invention obviate the need to have a particular barrel shape or configuration for mounting a needle assembly thereto. Another desirable feature of the present invention is to provide a relatively simplified needle assembly which comprises fewer components, thereby providing a user-friendly and safe retractable syringe while keeping manufacturing costs to a minimum and/or facilitating mass distribution of retractable syringes. Embodiments of the present invention also provide configurations that allow the use of standard, commercially-available components, which may reduce overall manufacturing costs, streamline assembly processes, and avoid regulatory concerns often associated with non-standard materials and components. Additionally, the invention provides efficient delivery of fluid contents, thereby minimizing wastage of fluid contents, and/or integrates one or more locking systems to prevent or at least minimize syringe re-use and/or needle stick injury.

Throughout this specification, unless otherwise indicated, "comprise," "comprises," and "comprising," or related teens such as "includes" or "consists of," are used inclusively rather than exclusively, so that a stated integer or group of integers may include one or more other non-stated integers or groups of integers. As will be described further below, embodiments of the present invention may include one or more additional components which may be considered standard components in the industry of medical devices. The components, and embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein.

DETAILED DESCRIPTION

Figure 1:
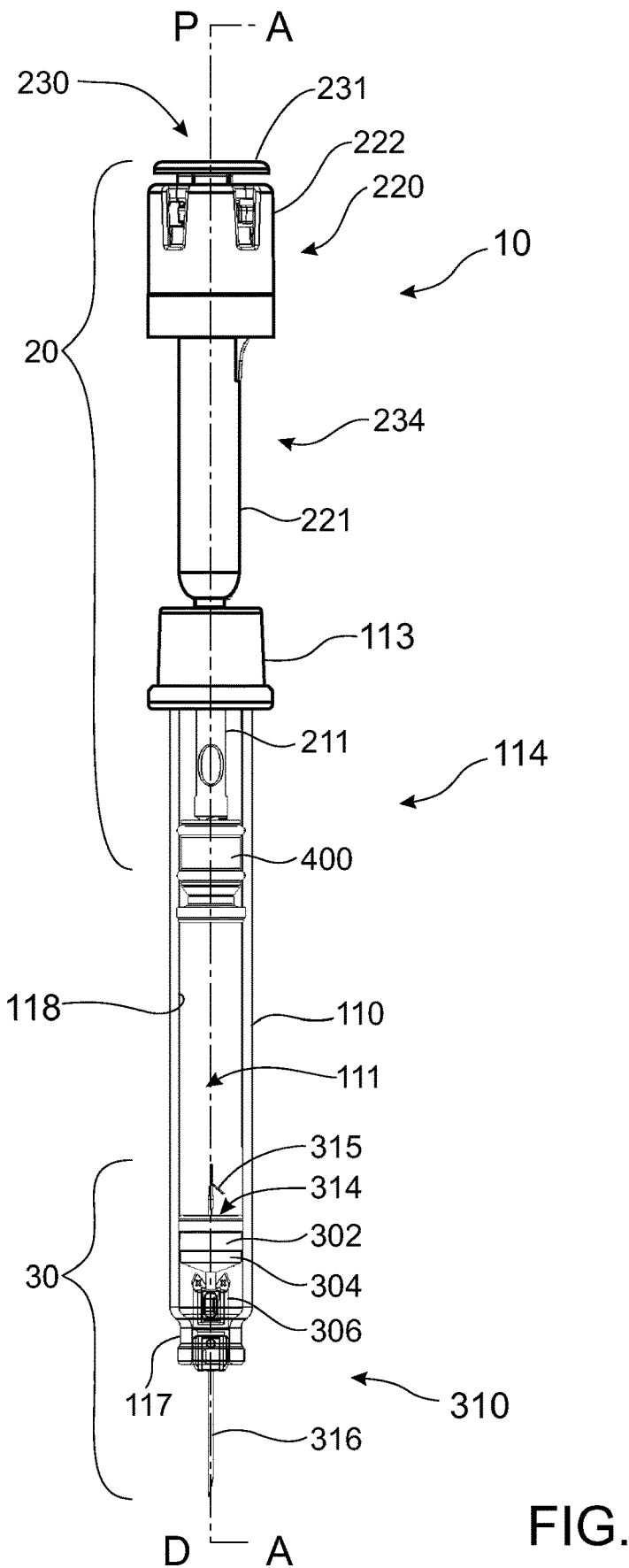
FIG. 1 is an isometric view of a first embodiment of a safety syringe according to the present invention.

The embodiments of the present invention provide reliable needle retraction, for improved user safety, without requiring complex manufacturing processes or operational changes for pharmaceutical companies or contract drug fillers. The embodiments of the present invention provide for a relatively simplified needle assembly which comprises fewer components, thereby providing a user-friendly and safe retractable syringe while keeping manufacturing costs to a minimum and/or facilitating mass distribution of retractable syringes. The novel needle assemblies of the present invention are notably able to be adapted to primary drug barrels of varying configurations and materials such as, preferably, straight-barrel glass barrels to provide integrated needle assemblies and retraction mechanisms to the barrel. Such embodiments may be utilized for pre-filled or fill at time-of-use injectable drug syringes. As such, the adaptable retraction mechanisms of the present invention may be flexibly attached, affixed, mounted, or otherwise mated to standard barrels, such as straight-glass barrels. As such, the needle assemblies may be connected to a standard straight-barrel drug chamber by having at least a proximal portion of the adapter inserted into and attached, affixed, mounted, er otherwise mated to the distal end of the barrel. The novel needle assembly designs of the present invention therefore obviate the need to have a particular barrel shape or configuration for mounting a needle assembly thereto. Of course, non-straight barrels may be utilized with the needle assemblies of the present invention as well, as will be described further herein. Accordingly, the shape of the needle assembly or certain components thereof may be configured to mate with a range of barrels to provide the reliable needle retraction safety syringes of the present invention.

The needle assemblies of the present invention may be selectable at the time of use or pre-attached to the barrel during manufacturing. In the selectable option, the design and configuration of the present invention allows a user to select a needle and/or needle assembly of a particular design or dimensions and adapt it to a syringe barrel for drug delivery. For example, the needle assemblies may be configured to provide a number of different needle lengths or thicknesses. The user may then select the needle assembly with their desired needle dimensions and adapt it to a syringe to deliver the drug. In the embodiments shown in FIG. 1, the needle assembly is directly mounted to the barrel. One or more additional components may be utilized to provide this adaptive feature. For example, one or more connecting components may be utilized to connect a barrel tip aspect of the needle retainer of the needle assembly to the barrel. In one such embodiment, one connecting component (such as a receiving component) may be fixedly mounted on a distal end of a glass barrel. The receiving component may directly receive and engage the barrel tip with the integrated retraction mechanism. Alternatively the needle assembly may include an additional connecting component (such as a mating component) which is used to engage the receiving component. Other optional components, such as elastomeric seals, which are known to one having ordinary skill in the art, may be necessary and incorporated into the device to facilitate the connection between the needle assembly and the barrel. The needle assemblies, while including essentially the same components regardless of needle dimensions, may be customized to facilitate the complete retraction of the needle into the barrel. For example, longer biasing members (e.g., longer springs) may necessarily be selected or modified to facilitate retraction of a longer needle, as would be readily appreciated by one ordinarily skilled in the art.

The embodiments of the present invention provide configurations which may also utilize materials and components which are readily employable for pharmaceutical use many of which are increasingly considered off-the-shelf or standard components. This reduces overall manufacturing costs, streamlines assembly processes, and avoids unnecessary regulatory concerns often associated with the use of non-standard materials and components. Additionally, the present invention provides components and devices which are aesthetically-similar to conventional syringes, which do not have needle retraction mechanisms, are ergonomically attractive to end-users, such as a medical practitioners and self-administering patients, and provide highly desired integrated safety features. These embodiments, accordingly, provide novel and cost-efficient components and devices which are readily integrated into drug filling processes.

Furthermore, the embodiments of the present invention provide efficient delivery of fluid contents, thereby minimizing wastage of pharmaceutical drugs. They similarly provide configurations which minimize dead-space, e.g., interstitial voids within the syringe barrel, which reduces or eliminates the capture of undesirable air bubbles during the assembly or filling process. These aspects of the present invention may provide highly desired functional and aesthetic characteristics, and may be modified to produce a range of different configurations.

The syringes of the present invention enable drug delivery with integrated safety as they prevent accidental exposure to the needle, as is common with needle stick injuries. As described above and detailed in the figures, a user may utilize the safety syringes of the present invention to perform the stages of drug delivery, including: needle insertion, drug dose delivery, needle capture, retraction activation, and needle retraction. Notably, the components of the needle assembly of the present invention are held substantially in position through the stages of needle insertion and drug dose delivery. This novel feature enables the barrel to be graduated, i.e., marked with volumes, because the reference point for end of dose is constant. The substantially stable and constant position of the needle seal through the stages of needle insertion and dose delivery, the stages during which some amount of drug may still reside in the drug chamber of the barrel, enables the identification of "zero volume," i.e., the point where there is no drug left in the chamber. Moving proximally from this point along the axial length of the barrel, drug volumes can be calculated based on the diameter of the barrel and can be marked along the length of the barrel. Several methodologies exist for measuring volumes and marking graduations on cylindrical barrels, which are known to one having ordinary skill in the art. Accordingly, the novel design of the needle assemblies and syringes of the present invention enable the use of graduated syringe barrels. This is a desirable feature for syringe users, including medical professionals and patients.

By integrating one or more locking systems to prevent or at least minimize syringe re-use and/or needle stick injury, the embodiments of the present invention provide highly desirable products which are cost-efficient to manufacture and easy-to-use by medical practitioners and self-administering patients. Such locking systems may include, for example, needle retraction mechanisms and/or arrangements that block a retracted needle from again extending from the end of the syringe. The novel features and functionality of the needle assemblies and syringes of the present invention provide a number of safety advantages to the user. For example, the locking mechanism may be configured to provide visual, audible, and/or tactile feedback to the user that the drug dose has been fully delivered, the retraction mechanism has been activated, the needle has been retracted, and that the syringe is safe for disposal. The components of the present invention are also configured such that there is increased destruction of the components, and the syringe overall, at the end of use. Such integrated safety and destruction prevents the reusability of the syringe and increases the safety profile of the device. For example, an optional needle block may be configured to prevent the needle from translating in the proximal direction out of the barrel tip after needle retraction. Additionally or alternatively, one of the existing components may function as a needle block after retraction of the needle has occurred, as described further herein. Depression of the plunger rod and axial translation of the needle in the distal direction after retraction, in this configuration, will result in the needle becoming bent within the barrel as a force is applied by the user. Another safety feature enabled by the present invention is the ability to control the rate of retraction of the needle. Controlled needle retraction prevents injury to the patient after the drug dose has been delivered. This can be facilitated by active components, such as one or more friction members limiting the rate of expansion of the biasing member upon retraction activation, or by passive components, such as the selection of biasing members which have slower expansion. In the embodiment shown in FIG. 1, the retraction is controlled by plunger rod and plunger seal. At the end of dose, upon activation of needle retraction, the user is still in contact and applying force to the proximal end of the plunger rod. As the biasing member is caused to expand, it imposes an axial force in the proximal direction to retraction the needle and/or needle assembly. This action conveys the force to the plunger seal, which is in contact with the needle seal at the end of dose, and the plunger rod. The friction caused by the needle seal and the plunger seal against the interior of the barrel limits the rate of retraction of the needle assembly. As the user reduces the force they apply on the plunger rod, they can also control the rate of needle retraction. This controlled retraction is highly desired by syringe users as it increases the safety and reduces the pain felt to the patient.

The embodiments of the present invention are detailed further herein with respect to the attached figures. It is to be understood that these are merely non-limiting embodiments and that other similar embodiments are within the contemplation of the present invention and within the breadth and scope of the present disclosure.

As used herein to describe the syringe, barrel, needle assembly, or any of the relative positions of the components of the present invention, the terms "axial" or "axially" refer generally to a longitudinal axis "A" around which syringe or barrel is preferably formed although not necessarily symmetrically there-around. The term "radial" refers generally to a direction normal to the axis "A". The terms "proximal," "rear," "rearward," "back," or "backward" refer generally to an axial direction in the direction of P shown in FIG. 1. The terms "distal," "front," "frontward," "depressed," or "forward" refer generally to an axial direction in the direction of D shown in FIG. 1. It is to be understood that the term "spring" is used herein to suggest a biasing member, such as a substantially spiral-wound coil, that may be compressed and allowed to expand in a given direction. While the spring element such as the arrangement discussed and utilized in the embodiments detailed herein may be utilized, it is within the contemplation of the present invention that other types of biasing members may be readily employed for the same purpose while remaining within the breadth and scope of the present invention. For example, springs such as compression springs, torsion springs, constant force springs, extension springs, and leaf springs, or combinations of different types of springs may be utilized within the scope of the present invention, as would be understood by an ordinarily skilled artisan. Additionally or alternatively, biasing members other than springs may also be employed for similar purposes. Non-limiting examples of biasing members include a spring, elastic or other device for storing releasable energy. In at least one embodiment, however, the biasing member is preferably a spring, such as a compression spring.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be resoftened to their original condition by heat; thermosetting polymers cannot. As used herein, the term "plastic" refers primarily to moldable thermoplastic high polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or rubbery elastomers that are approved for use in applications where they are in direct contact with therapeutic liquids that can interact with plastic or that can be degraded by substituents that could otherwise enter the liquid from plastic. As used herein, the term "elastomer," "elastomeric" or "elastomeric material" refers primarily to crosslinked thermosetting rubbery polymers that are more easily deformable than plastics but that are approved for use with pharmaceutical grade fluids and are not readily susceptible to leaching or gas migration. As used herein, the term "fluid" refers primarily to liquids, but can also include suspensions of solids dispersed in liquids, and gasses dissolved in or otherwise present together within liquids inside the fluid-containing portions of syringes.

Additionally, the needle assemblies of the present invention utilize materials that are substantially non-reactive with therapeutic fluids or drugs, and are suitable for use in pharmaceutical grade applications. The novel needle assemblies are configured to minimize or eliminate the possibility of contact or interaction between degradable materials, such as certain plastics, with the therapeutic fluids or drugs. The needle assemblies, with adaptable needle retention and retraction mechanisms, also provide fluid pathways from the primary drug chamber to the patient, through the needle, which are substantially absent of degradable materials. Such novel adapter configurations, when integrated into barrels to provide the novel safety syringes of the present invention, provide increased stability and shelf-life parameters to the drug and drug delivery devices. These characteristics are thought to be highly desirable for generally all pharmaceutical treatments, but perhaps especially of value in syringes for use with biologics and other complex therapies. In one embodiment, for example, a metal needle is retained within a glass barrel by an elastomeric needle seal at a proximal end of the needle and by an aperture of a plastic barrel tip at a portion of the needle that is distal to the needle seal, such that the drug fluid pathway contains (and the drug contacts) only glass, elastomer, and metal, without contacting any plastic, as the drug travels from drug chamber to patient. In other embodiments, other material combinations or fewer materials may be utilized for the drug fluid pathway.

One or more embodiments of the present invention may further include certain standard components. For example, the needle assembly configurations and syringe devices of the present invention may include one or more O-rings. In at least one embodiment, one or more O-rings are employed to seal the barrel tip within the barrel and/or to ensure a sterile environment and container integrity within the drug chamber of the barrel.

Additionally or alternatively, the needle assembly may include one or more controlling members to facilitate the control of the rate of retraction. Similarly, the needle assembly may include one or more needle blocks, such as clips, flaps, flanges, or the like, which function to prevent the needle from being translated or protruding out of the barrel through the aperture of the barrel tip after the retraction mechanism has been initiated or completed.

Furthermore, the safety syringe may include one or more components for aesthetics, ease-of-use, or other purposes. For example, one or more embodiments of the present invention may include a finger flange. The finger flange may be pre-formed along any portion of the barrel or safety syringe, or may be a separate component that is connected to or affixed to the barrel or safety syringe. In at least one embodiment, the finger flange is a preformed component at the distal end of the barrel. The finger flange may be configured to allow a user to rest their pointer and middle fingers on the flange, and may provide a leverage interface when the user is depressing the plunger with their thumb for injection of the drug. The position, shape, number, and materials for such components may vary, as would be readily appreciated by a skilled artisan, to meet any number of desired characteristics.

Similarly, while the components of the needle assembly and the safety syringe are described herein as separate components, it is within the contemplation of the present invention that certain groups of these components may be combined to form a single component capable of performing the functions of the individual components. Additionally, as would be appreciated by one having ordinary skill in the art, the components of the safety syringes may be manufactured as individual components or as single components. As described above, the finger flange may be a component that is pre-formed, during the manufacturing process, as a part of the barrel itself. Accordingly, in at least one embodiment, the finger flange may be a glass finger flange extension of the barrel.

Furthermore, while the components of the needle assembly are described herein as separate components, they may be unified components having multiple functions. As discussed above, the biasing member (e.g., spring) may be compressed in its energized state and the locking mechanism engaged either prior to installation in the barrel tip or after the components have been mounted in the barrel. The configuration of the components and their assembly may vary based on the assembly process, the device parameters, and other desired characteristics.

FIG. 1 shows an isometric view of one embodiment of a safety syringe 10, according to the present invention. In accordance with the invention, a needle assembly 30 is provided for attachment to a syringe barrel 110 having a plunger assembly 20. Barrel 110 further comprises barrel tip 117 at a distal end thereof and internal wall 118 which, together with plunger 20 defines internal chamber 111. Barrel 110 further comprises proximal end 114 that comprises release ring 113, which will be described in more detail hereinafter. The barrel 110 may be a plastic barrel, a glass barrel, or made of any other known material for use in medical devices. The barrel 110 may be tapered, non-cylindrical, or substantially straight. In an embodiment preferred for manufacturing purposes, the barrel 110 is a straight barrel glass cylinder. The embodiments of the present invention also enable significant other advantages in the marketplace for safety syringes.

For example, one or more embodiments can utilize standard components, such as standard plunger seals and rigid needle shields, thereby greatly reducing the need for specially-tailored or injection molded components. For example, FIG. 1 shows an embodiment which utilizes a standard plunger seal 400 and a rigid needle shield (not shown), among other possible standard components. The plunger seal 400 may be, for example, an ethylene tetrafluoroethylene (ETFE) coated rubber stopper/seal, such as that which is readily-available under the trade name "FluroTec" from West Pharmaceutical Services, Inc., of Lionville, Pa. Other components may similarly be standard, off-the-shelf components, providing a great advantage of the embodiments of the present invention. This advantage of the embodiments of the present invention provides valuable manufacturing efficiencies and operational cost-savings.

Figure 2A:
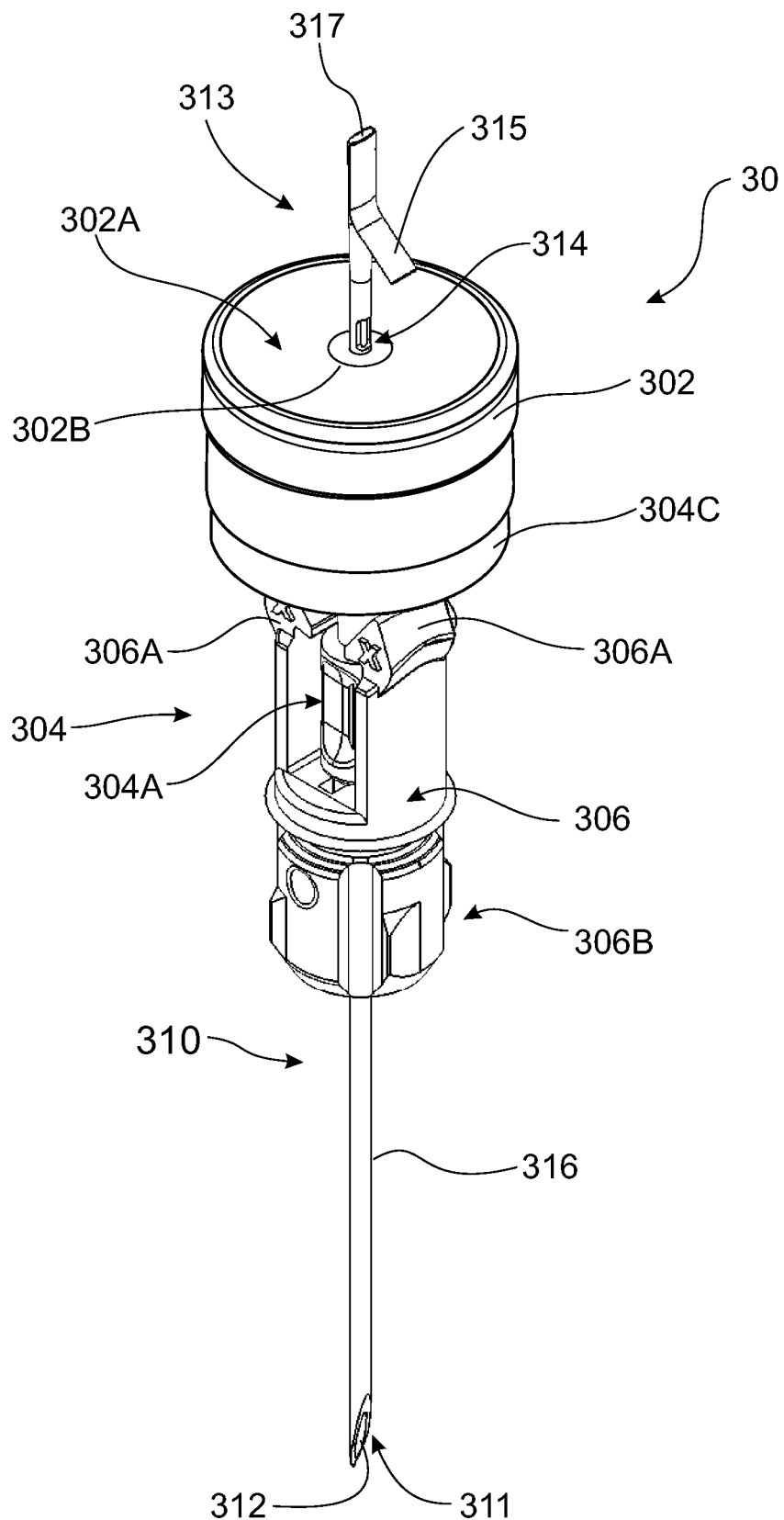
FIG. 2A is an enlarged isometric view of the needle assembly component of the embodiment shown in FIG. 1.
Figure 2B:
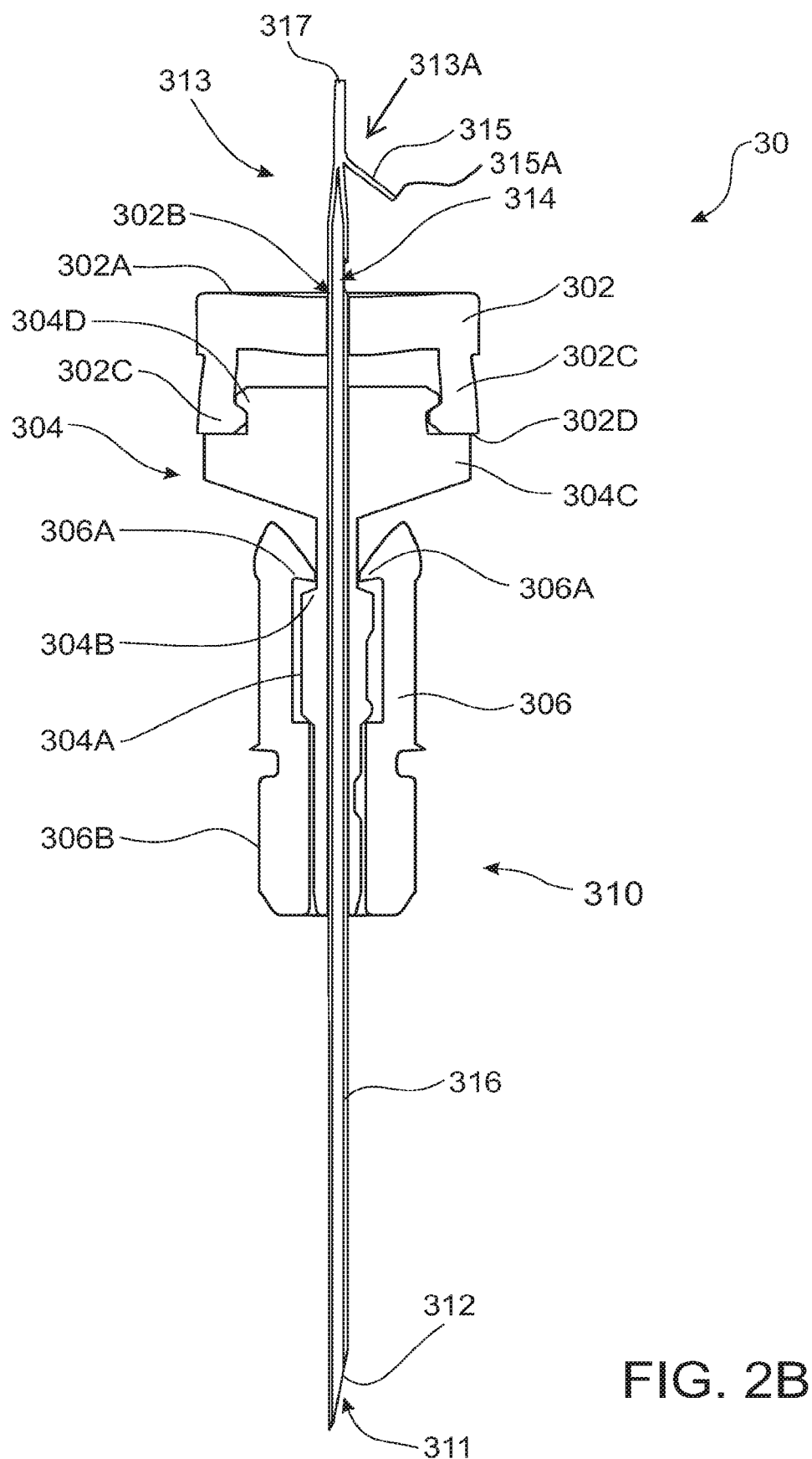
FIG. 2B is a cross-sectional view of the needle assembly shown in FIGS. 1 and 2A.

Referring also to FIGS. 2A and 2B, needle assembly 30 facilitates mounting of a retractable needle 310 to the syringe barrel 110. The needle assembly 30 includes a retractable needle 310 having cannula 316 that has delivery tip 311 comprising delivery aperture 312 and proximal end 313 having plunger-engaging member 313A, inlet aperture 314, proximal tip 317 and plunger-engaging projections 315. Inlet aperture 314 at proximal end 313 of cannula 316 is located distally of the plunger-engaging projections 315. Proximal end 313 of cannula 316 further comprises proximal tip 317 capable of puncturing plunger seal 400 so that the plunger-engaging projections 315 can be subsequently engaged by the plunger seal 400. The plunger-engaging projections 315 are located between proximal tip 317 and inlet aperture 314.

Needle assembly further comprises needle seal 302, and needle retainer 306. Cannula 316 at least partially passes through proximal surface 302A of needle seal 302 at a substantially axial aperture 302B. Cannula 316 is a hollow core cannula which comprises a fluid path from inlet aperture 314 at proximal end 313 to delivery aperture 312 of delivery tip 311 for fluid to pass therethrough. In other embodiments, there may be a plurality of delivery apertures 312 and/or inlet apertures 314 that may form multiple, separate fluid paths. Plunger-engaging projection 315 may comprise one or a plurality of barbs, prongs, hooks, or similar structures which permit capture of the retractable needle 310 by plunger 20 or plunger seal 400, as will be detailed further herein, for needle capture and retraction.

The needle retainer 306 comprises distal end 306B, cannula 316 extending through the distal end 306B of the needle retainer 306 for injection of a fluid, such as a medicament. The needle retainer 306 further comprises flex aims 306A that releasably engage ledge 304B of body portion 304A of needle overmould ("NOM") 304. In at least one optional embodiment, the needle-over-mold component ("NOM") 304 is fixedly attached to the needle 310. The NOM may be connected to the distal surface 302D of the needle seal 302 and may travel, such as by being a couple component, with the needle 310 during the operation of the syringe. The NOM 304 may have a wider body portion 304A and a ledge 304B where the needle retainer 306 is removably or detachably engaged. As is described further herein, the needle retainer 306 may initially retain the NOM 304 and needle 310 in position for certain stages of syringe operation, such as needle insertion, and allow disengagement of the NOM 304 and retractable needle 310 from the needle retainer 306 during other stages of operation, such as needle retraction. Alternatively, these functions of the NOM may be performed by the needle 310 itself. For example, the needle 310 may optionally have prongs thereupon, such as welded prongs, that allow for removable engagement and disengagement of the needle 310 from the needle retainer 306. Accordingly, a supplemental component such as a NOM 304 is not necessary for such functions and may be optionally utilized.

Figure 3A:
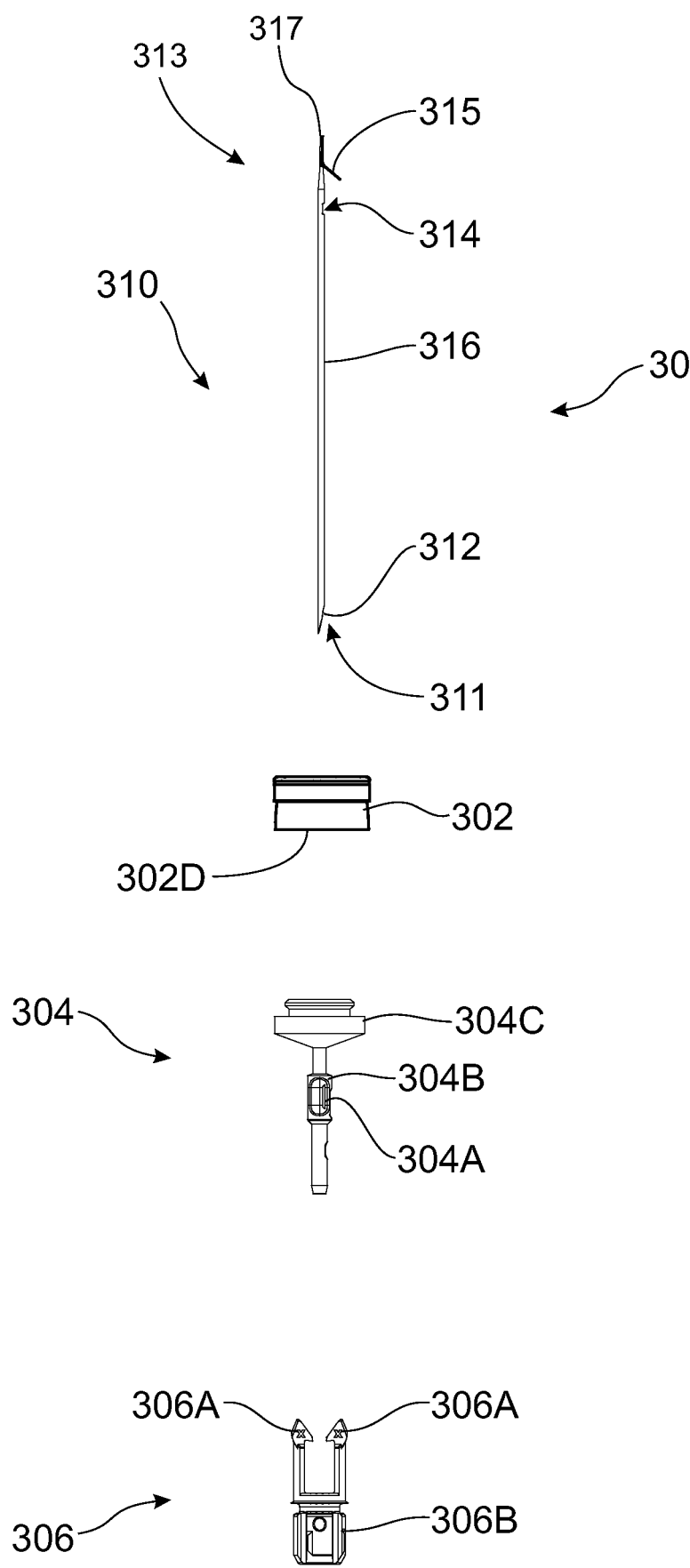
FIG. 3A shows an exploded view, along an axis 'A", of a needle assembly according to at least one embodiment of the present invention.
Figure 3B:
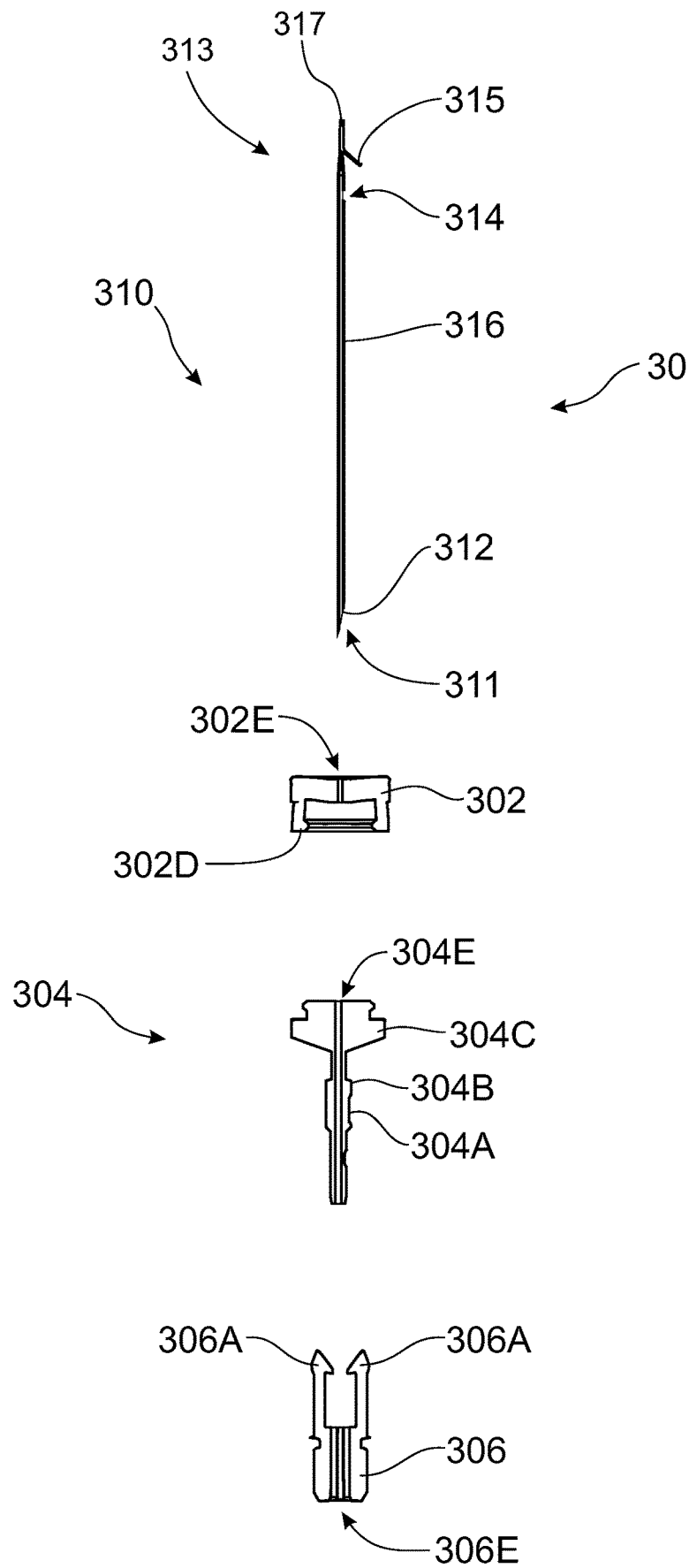
FIG. 3B shows a cross-sectional view of the needle assembly shown in FIG. 3A.

FIGS. 2A and 2B show enlarged and cross-sectional views of the needle assembly 30, according to at least one embodiment of the present invention, respectively. FIG. 3A shows an exploded view, along an axis 'A", of a needle assembly according to at least one embodiment of the present invention and FIG. 3B shows a cross-sectional view of the needle assembly shown in FIG. 3A. A previously described, optional NOM 304 is shown as an over-molded, co-molded, or fixedly attached component to needle 310. The NOM 304 may be attached to the needle seal 302 such that the two components move as one, or may be a co-molded, dual-shot, or otherwise formed aspect of the needle seal 302. The NOM has a head 304C which engages the needle seal 302 by way of base rim 302C engaging waist 304D. NOM 304 further comprises body 304A and ledge 304B which detachably engage the needle retainer 306. As evident from FIGS. 3A and 3B, NOM 304, needle seal 302 and retainer 306 comprise respective internal bores 304E, 302E and 306E through which cannula 316 passes to create a fluid pathway from inlet aperture 314 to delivery aperture 312 for drug delivery from delivery end 311 of cannula 316. The needle assembly 30 may then be integrated into a barrel 110 to produce a safety syringe 10.

The needle assembly 30 may be mounted to the syringe barrel 110 by any appropriate coupling arrangement, as will be understood by those of skill in the art. For example, the needle assembly 30 may be coupled to the syringe barrel 110 by a coupling structure that may be separate from components of the needle assembly 30 and syringe barrel 110, or integral with the needle assembly 30 and the syringe barrel 110. As an advantage of the embodiments of the present invention, distal end 306B of needle retainer 306 of the needle assembly 30 may be configured to mate with any standard barrel 110 by any appropriate method. Moreover, the needle assembly 30 may be coupled to the syringe barrel 110 during the syringe manufacturing process or just prior to use. By way of example only, the distal end 306B of the needle retainer 306 may be coupled to the syringe barrel 110 by an interference fit, glue, or the like during the syringe manufacturing process. Alternately, for example, the syringe barrel 110 and needle assembly 30 may include mating threads or a Luer locking arrangement, such that the needle assembly 30 may be coupled to the syringe barrel 110 just prior to use.

FIGS. 4A-4E show cross-sectional views of the safety syringe shown in FIG. 1, as it progresses through the stages of operation including: needle insertion, dose delivery, needle capture, retraction activation, and retraction complete, respectively. FIGS. 4A-4E show corresponding enlarged views. The safety syringe 10 according to one embodiment of the present invention includes a barrel 110 having a needle assembly 30 attached or otherwise mounted at a distal end and a plunger assembly 20 attached or otherwise mounted at a proximal end. An optional release ring 113 at may also be attached at the proximal end 114 of barrel 110 to engage the plunger assembly 20, as is described further herein. A medicament, drug or pharmaceutical compound may be contained in chamber 111 of barrel 110 proximally of the needle seal 302. As would be appreciated by an ordinarily skilled artisan, the drug may be a solution, a powder, a suspension, or the like, or any combination thereof. As shown previously in FIGS. 3A and 3B, needle seal 302 may have aperture 302E pass-through at its center (e.g., at substantially the longitudinal axis of these components and the barrel 110). Aperture 302E may have a diameter equal to the diameter of the needle 310, such that the needle 310 is retained in position within the needle seal 302 during an initial needle insertion stage and allowed to axially translate in the proximal direction upon activation of the retraction mechanism. Alternatively, the needle seal 302 may not initially have an aperture prior to positioning of the needle 310 within the needle seal 302 at assembly. In this configuration, the needle 310 may be pushed through the needle seal 302 at assembly and create a line-to-line or interference fit, thereby ensuring a tight seal between the components and minimal or no dead-space. In the later configuration, a NOM 304 may be attached to the needle 310 after the needle 310 is caused to at least partially pass through the needle seal 302.

Figure 4A:
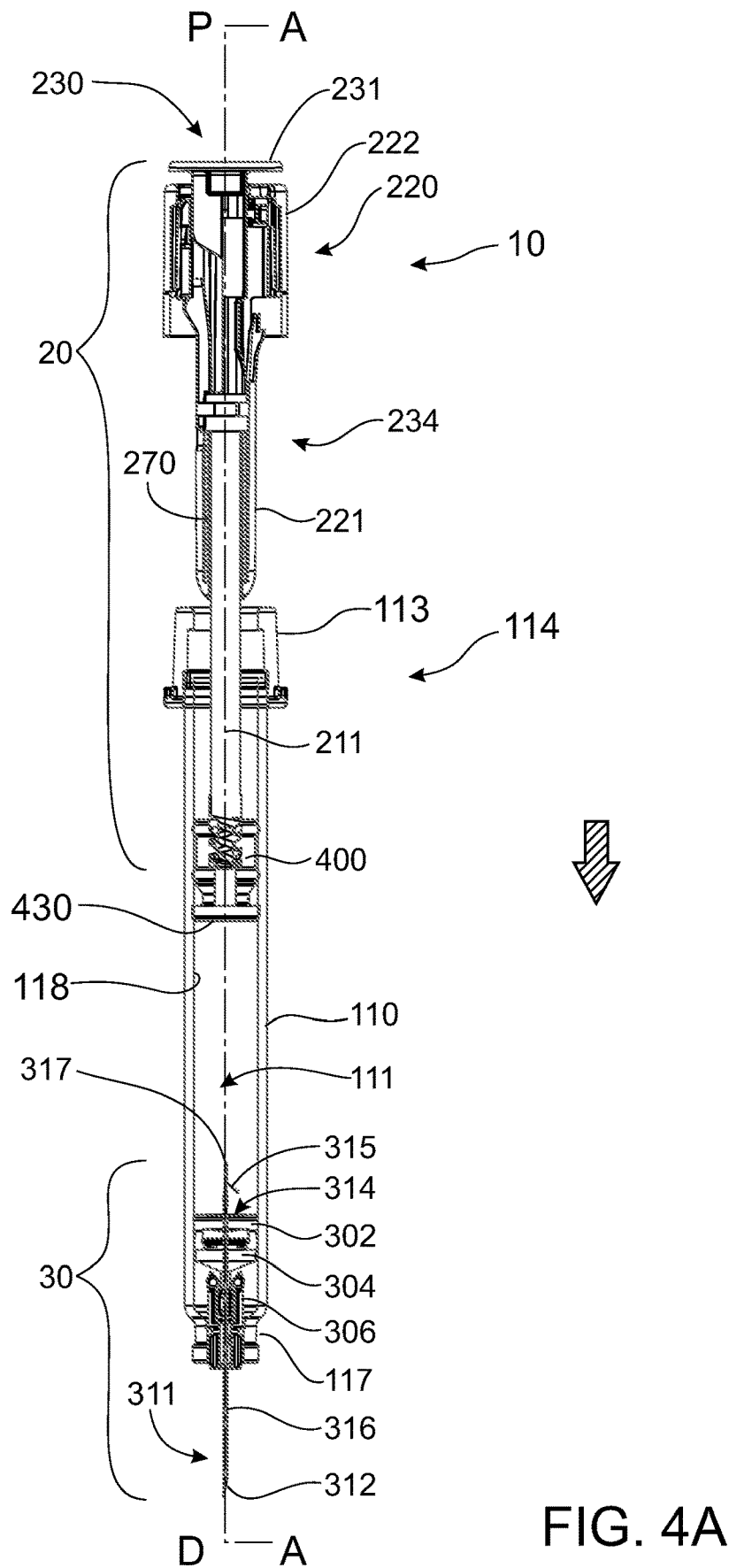
FIGS. 4A-4E show cross-sectional views of the safety syringe shown in FIG. 1, as it progresses through the stages of operation including: needle insertion, dose delivery, needle capture, retraction activation, and retraction complete, respectively.
Figure 5A:
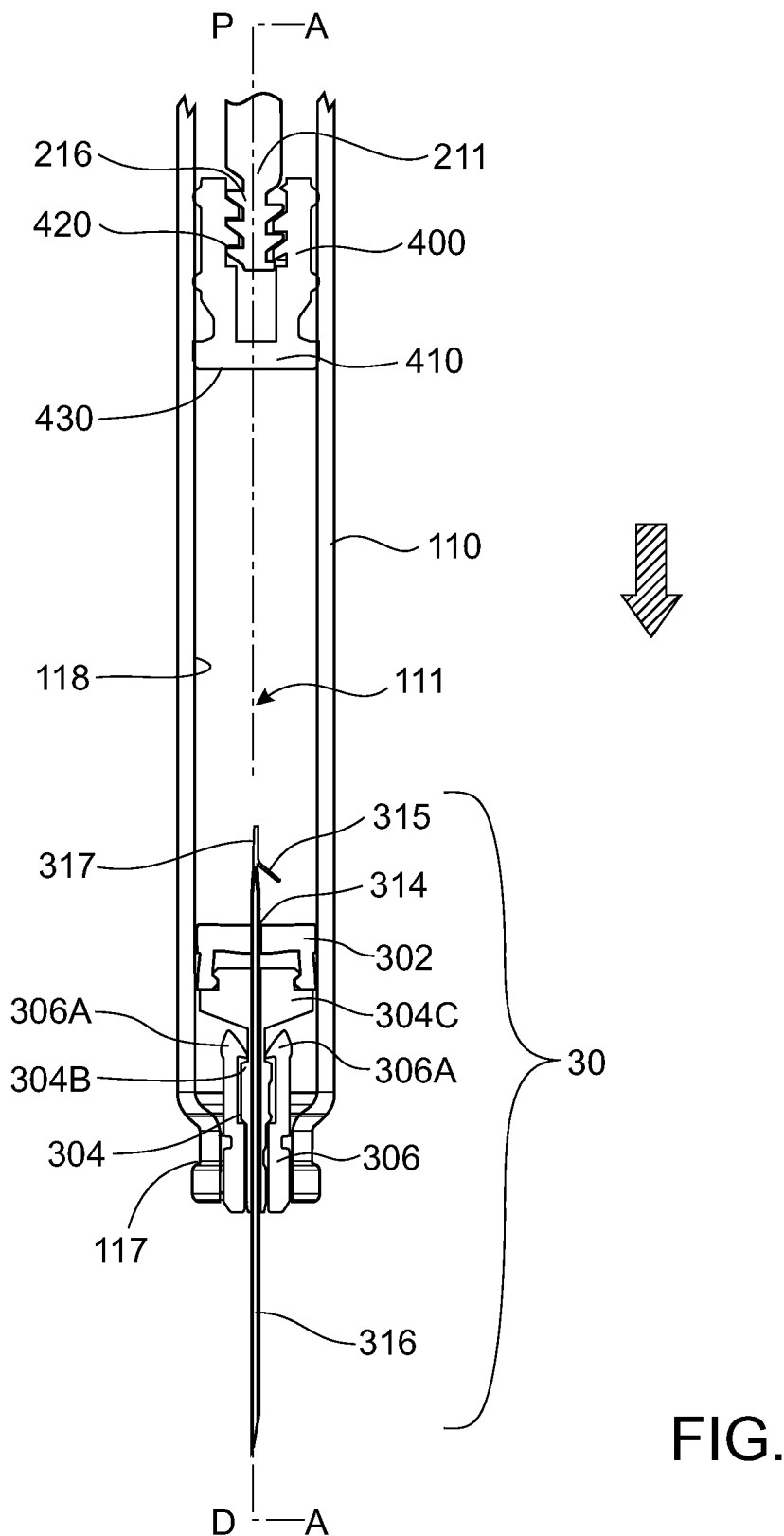
FIGS. 5A-5E show enlarged cross-sectional views of the safety syringe shown in FIGS. 1 and 4A-4E, as it progresses through the stages of operation including: needle insertion, dose delivery, needle capture, retraction activation, and retraction complete, respectively.

FIGS. 4A and 5A show the safety syringe 10 in an initial configuration for needle insertion. As shown in FIG. 4A, the needle assembly 30 may be inserted through the proximal end of the barrel 110 and then attached at the distal end of the barrel 110, such as by a glue, adhesive, snap-fit, or interference fit, for example. This may be particularly useful when a tapered or non-straight barrel is utilized. Alternatively, the needle assembly 30 may be attached directly to the barrel 110 at least partially through or at the distal end of the barrel 110. That may be utilized for attachment to straight barrels, as described above. FIG. 4A shows the needle assembly 30 assembled to a barrel 110. The interior portion of the barrel 110 just proximal to needle seal 302 is generally defined as a drug chamber 111 within which a drug fluid may be filled for drug delivery. Certain standard optional components including a flange and a rigid needle shield ("RNS"), neither of which is shown, may be attached to finish assembly of the safety syringe. For example, the flange may be attached to release ring 113 while the RNS may be attached to the distal end of the barrel 110 to cover the exposed needle 310 prior to use of the safety syringe 10. A plunger assembly having a plunger seal 400 and plunger rod 211 may be inserted into the proximal end of the barrel 110 to complete the assembly of the safety syringe 10. With the RNS removed, as shown in FIGS. 4A and 5A, the needle 310 of the safety syringe 10 may be inserted into the body of the patient, such as subcutaneously or intramuscularly, for drug delivery. Upon needle insertion, the plunger assembly 20 may be depressed (in the direction of the hatched arrow) to force the contents out from internal chamber 111 through fluid path 310A of needle 310 for drug delivery. Accordingly, the plunger assembly 20 is axially, slidably movable in internal chamber 111 of barrel 110 to thereby deliver the contents of the internal chamber 111 and subsequently retract retractable needle assembly 30, as will be described further herein.

In at least one embodiment of the present invention, the plunger assembly is essentially similar to that described in either of International Publications WO2009/003234 or WO2011/075760. Preferably, in at least one embodiment of the present invention the plunger assembly is similar to that described in International Publication WO2011/075760, and will be briefly described as follows with reference to FIGS. 7-9. Plunger assembly 20 comprises plunger member 210 comprising plunger rod 211, annular ledge 212 and seal-engaging member 216, which in this embodiment is screw threaded, which engages complementary, screw-threaded recess 420 of plunger seal 400. Plunger seal 400 further comprises needle-engaging portion 410 and substantially planar or flat distal face 430 which can assist minimizing the complexity of plunger seal 400 for manufacture and subsequent use. Plunger 200 further comprises plunger outer 220 having elongate body 221 with base 225 and head 222 and locking member 227. Releasably connected with plunger member 210 is control rod 230 comprising button 231, arm 232 and shaft 233. Plunger assembly 20 further comprises compressed spring 270 which is mounted between plunger member 210 and plunger outer 220, held in an initially compressed state between ledge 212 of plunger member 210 and base 225 of plunger outer 220. In at least one embodiment, control rod 230 is releasably coupled to plunger member 210 by way of shaft 233 which is releasably connected to plunger member 210 by optional frangible junction 234 (shown in FIGS. 8-9). Control rod 230 also releasably engages plunger outer 220 to thereby retain spring 270 in an initially compressed state held between annular ledge 212 of plunger member 210 and base 225 of plunger outer 220 in elongate portion 221. Initially, ledge 235 of arm 232 abuts rim 229 of plunger outer 220 to thereby retain control rod 230 and prevent axial movement of control rod 230 relative to plunger outer 220. However, arm 232 of control rod 230 is resiliently flexible and movable in the direction of the solid arrow shown in FIG. 7, which will allow disengagement of control rod 230 from plunger outer 220 to facilitate decompression of spring 270, as will be described hereinafter.

Figure 4B:
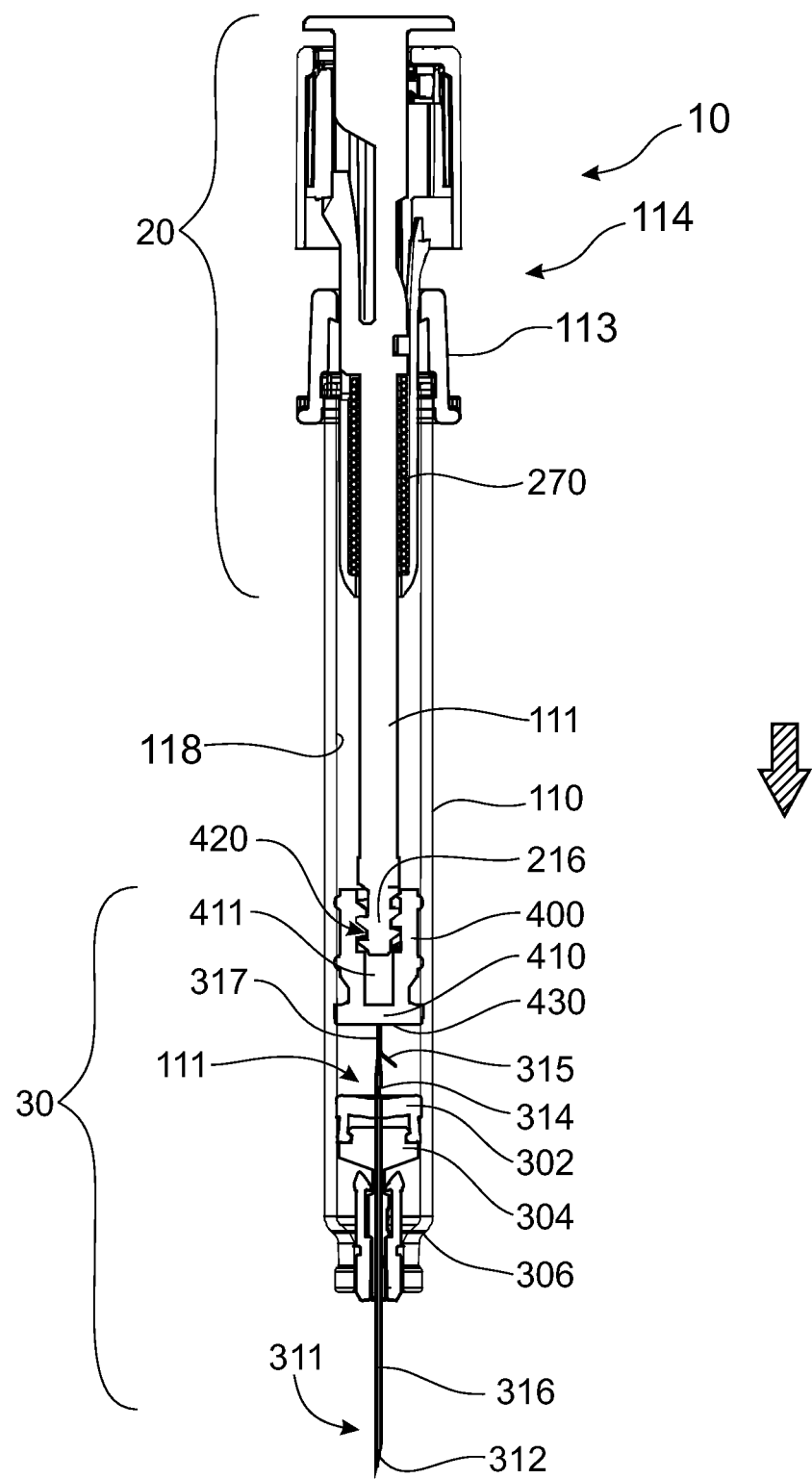
Figure 4C:
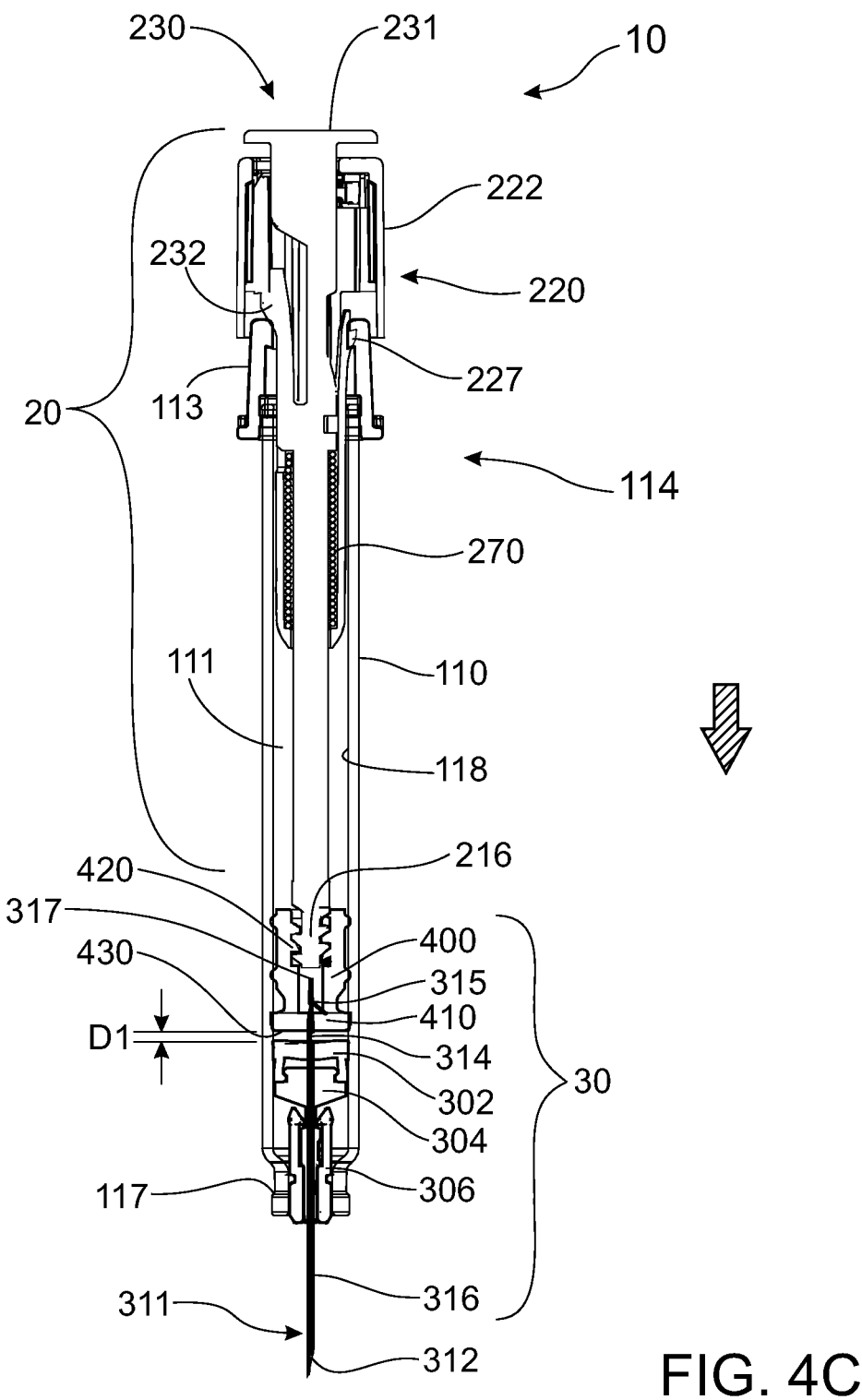
Figure 5B:
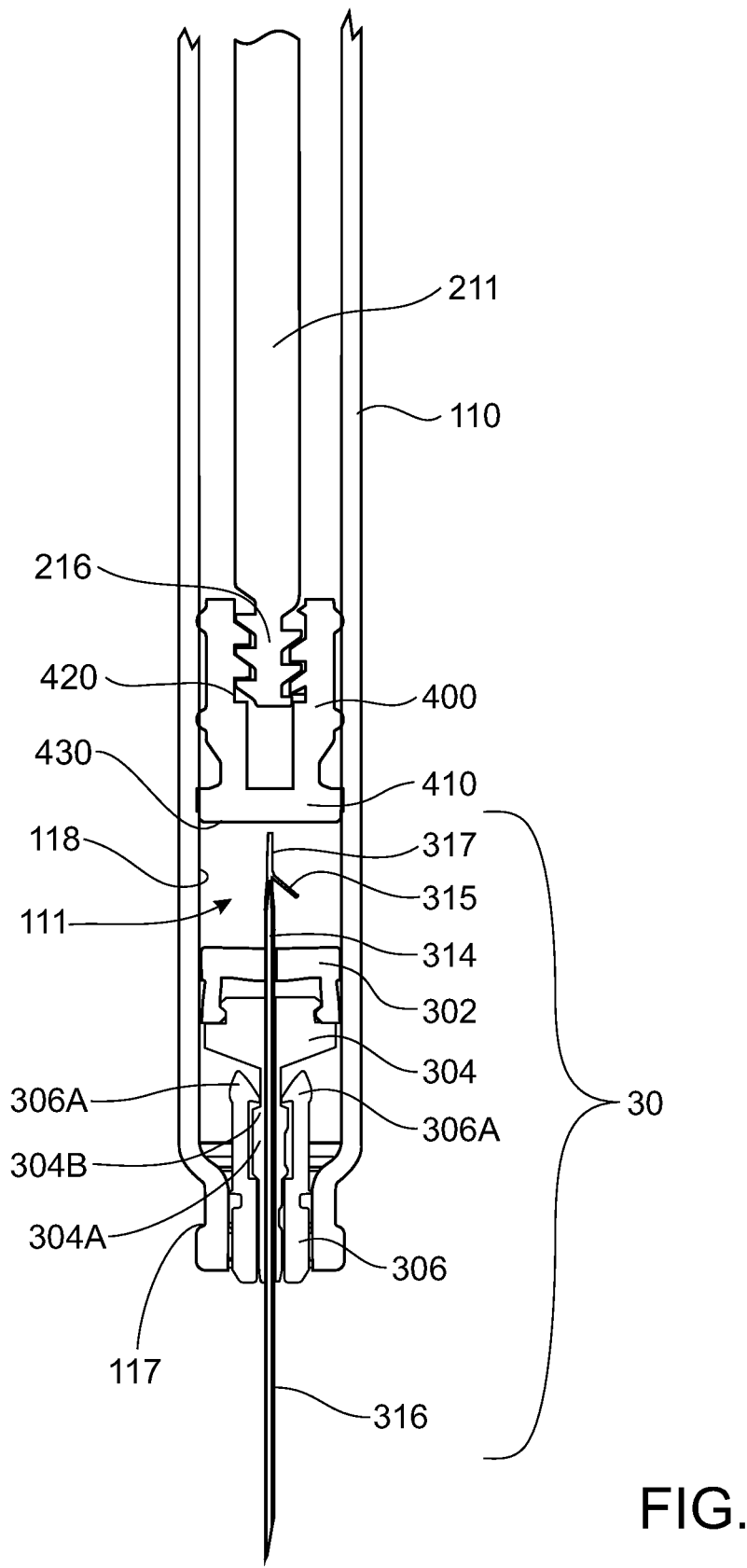
Figure 5C:
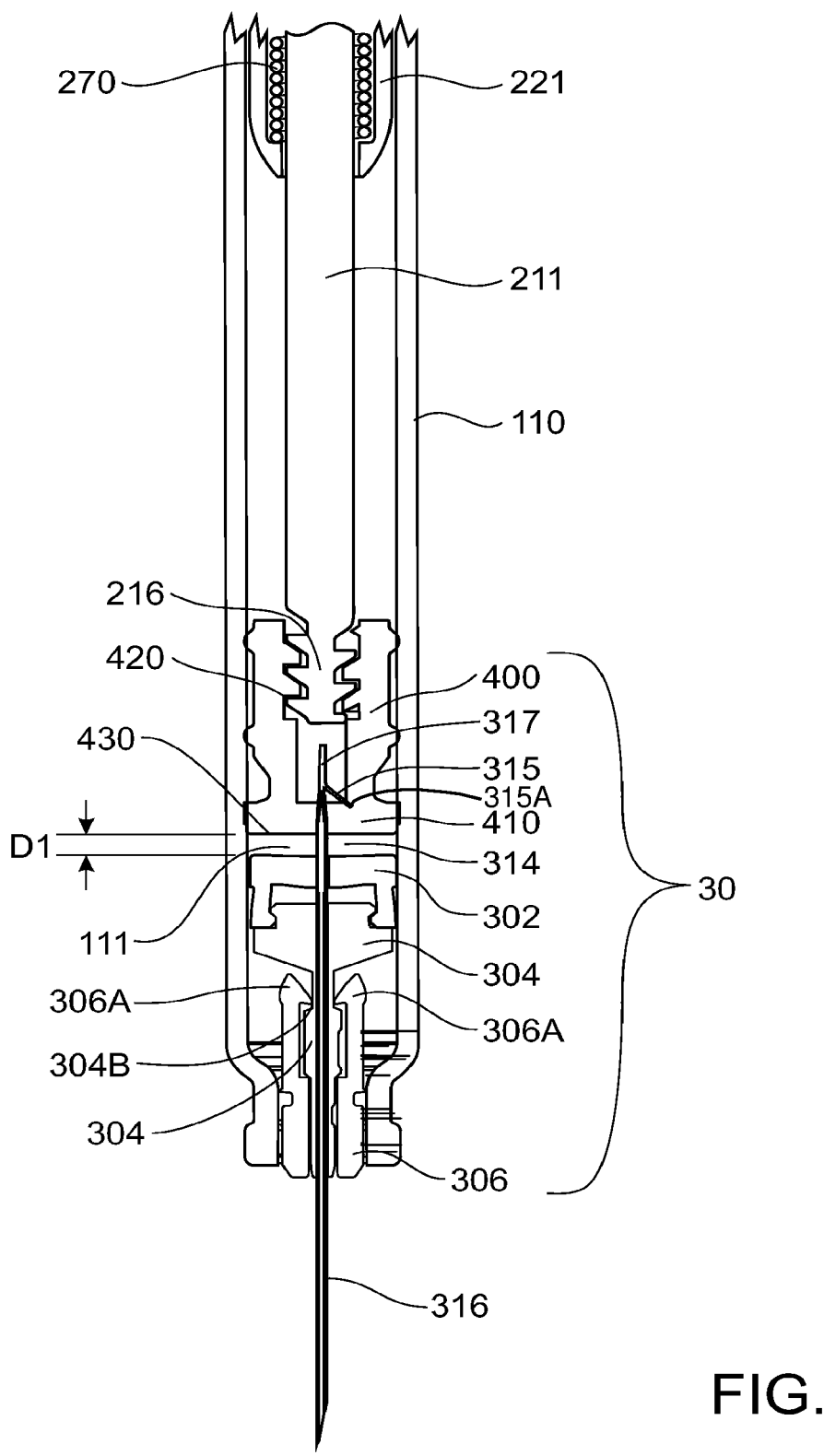
Figure 5D:
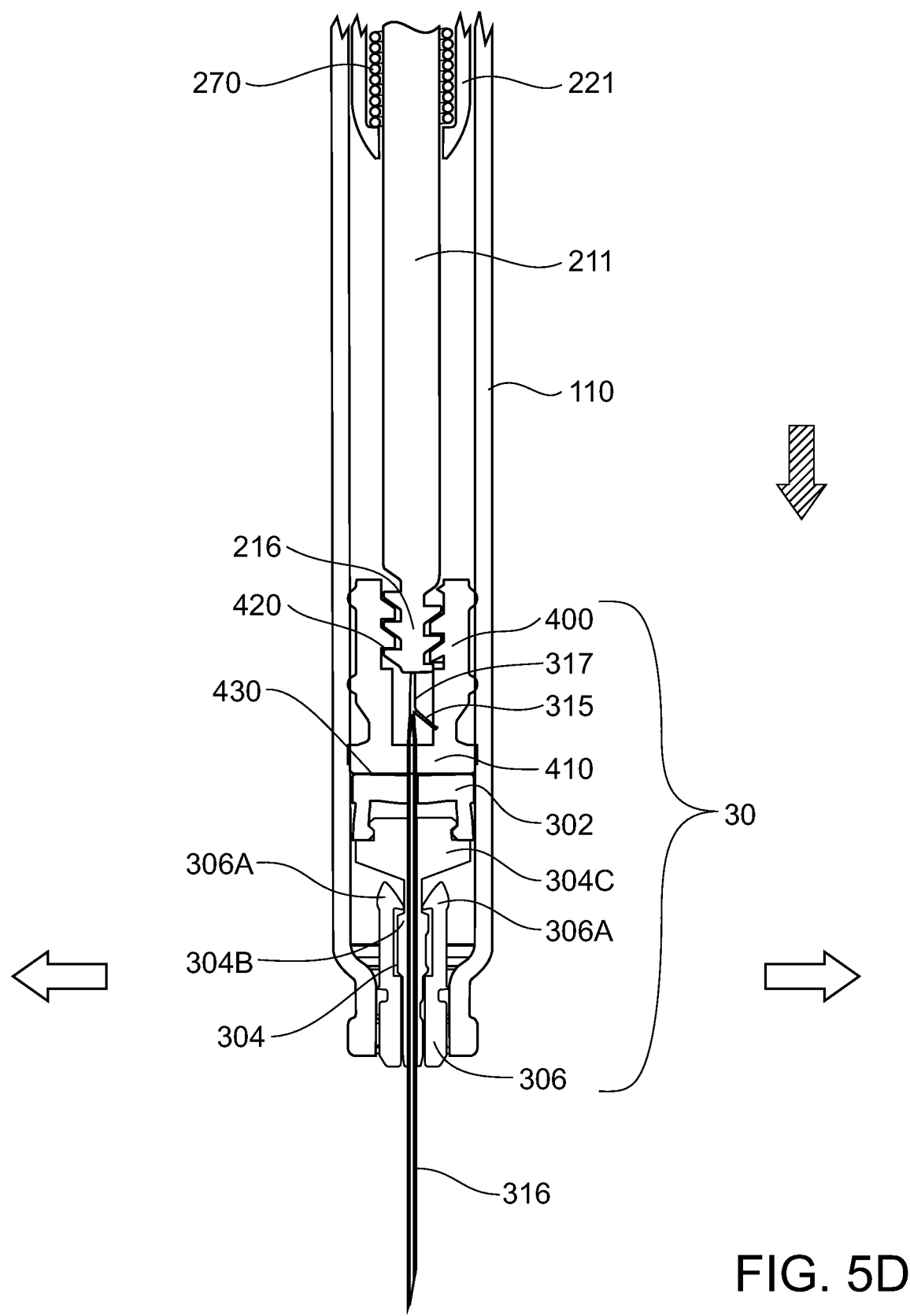

Needle assembly 30 includes retractable needle 310 having cannula 316, needle retainer 306, needle seal 302, and optional NOM 304. During delivery of fluid contents, plunger assembly 20 moves axially through barrel 110 in the direction of the hatched arrow in FIGS. 3B and 4B. As shown in FIGS. 4B and 5B, plunger seal 400 bears against proximal end of needle 310 as it nears completion of delivery. As shown in FIGS. 4C and 5C, upon further depression of the plunger assembly 20 to complete drug delivery the plunger seal 400 is pierced by the proximal tip 317 of cannula 316 such that one or more barbs 315A is caused to enter internal recess 411 in needle engaging portion 410 of plunger seal 400. By placement of at least one inlet aperture 314 substantially along, or just above, where the needle 310 contacts the needle seal 302, any remaining or residual amount of drug fluid within chamber 111 may be forced into inlet aperture 314 for delivery from delivery aperture 312 of cannula 316 by continued depression of the plunger assembly 20 after retractable needle 310 engagement has occurred. This additional travel is shown as distance D1 in FIGS. 4C and 5C after needle capture has occurred. The design or configuration of the plunger seal 400 may permit plunger seal flexion in order to allow for the final portion of travel required to activate the retraction mechanism. The inner portion 411 of the plunger seal 400 is designed to continue moving distally while the plunger seal distal outer edge 412 stay fixed against the proximal surface 302A or needle seal 302. Similarly, the needle seal 302 may be configured to permit flexion of the radially inward portions of the needle seal 302, such as at the axial aperture 302A, while the perimeter of the needle seal 302 remains in a fixed position against the inner wall 118 of the barrel 110 until retraction occurs.

Figure 4D:
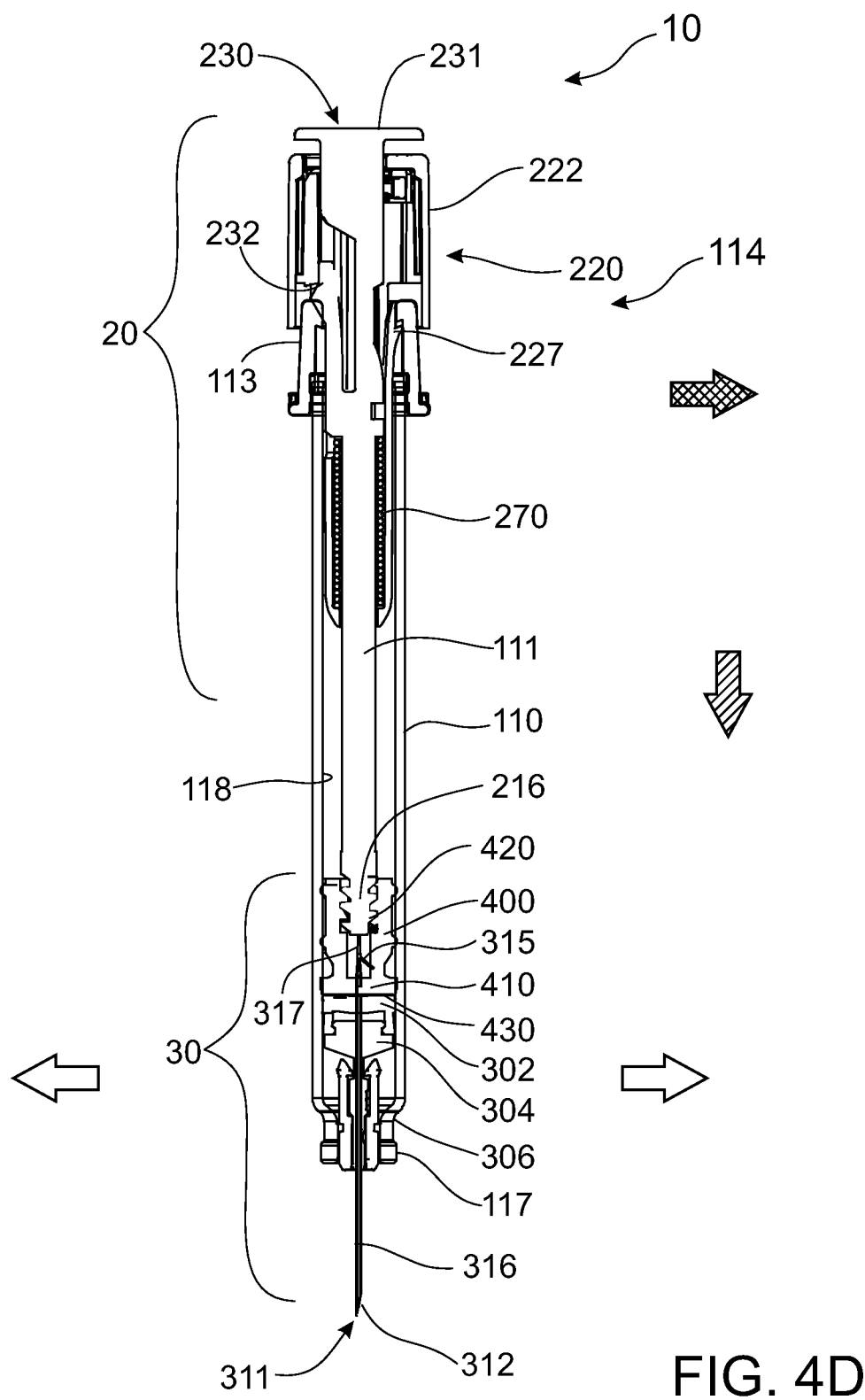

As the plunger assembly is further depressed or as the drug dose within the chamber 111 is substantially fully dispensed through the needle 310, the retraction mechanism is activated as shown in FIGS. 3D and 4D. As shown in the transition from FIG. 8 to FIG. 9, in order for retractable needle assembly 20 to retract at the end of delivery of fluid contents, compressed spring 270 must decompress, which is facilitated by plunger inner 210 disengaging from plunger outer 220. This disengagement is facilitated by release ring 113. As plunger inner 210 and plunger outer 220 are substantially fully depressed (i.e., axially translated in the distal direction as per the hatched arrow) to inject fluid from internal chamber 111, one or both may contact release ring 113. Through this contact, release ring 113 moves arm 232 radially inwardly (in the direction of the solid arrow) and out of engagement with rim 229 of plunger outer 220. This disengagement allows compressed spring 270 to decompress and push against ledge 212 of plunger inner 210 to thereby retract plunger inner 210 with control rod 230 coupled thereto. Plunger outer 220 remains substantially in contact or connection with release ring 113, while plunger inner 210, plunger seal 400, and needle 310 (by interaction between barb 315A and needle-engaging portion 410) are axially translated in the proximal direction by decompression of spring 270.

The force of this retraction is sufficient to overcome the flexingly detachable retaining force of flex arms 306A of needle retainer 306 acting upon body portion 304A and a ledge 304B of NOM 304. Release of the NOM from the needle retainer 306 is achieved passively through, for example, an angled contact between the flex aims 306A of the needle retainer 306 and ledge 304B on the NOM 304. This configuration permits the safety syringe 10 to function with a fixed needle seal 302, the benefits of which are described above. Accordingly, flex arms 306A are caused to flex outwards (in the direction of the hollow arrows in FIG. 4D and FIG. 6) and to slide off of, or otherwise disengage from, ledge 304B of NOM 304. When a NOM is not utilized, similar detachable engagement action may be utilized to disengage directly from aspects, such as welded aspects, of the needle 310 itself. A similar welded or otherwise preformed aspect of the needle 310 may be utilized to engage or contact the needle seal 302 entirely removing the need for an optional NOM 304.

Figure 4E:
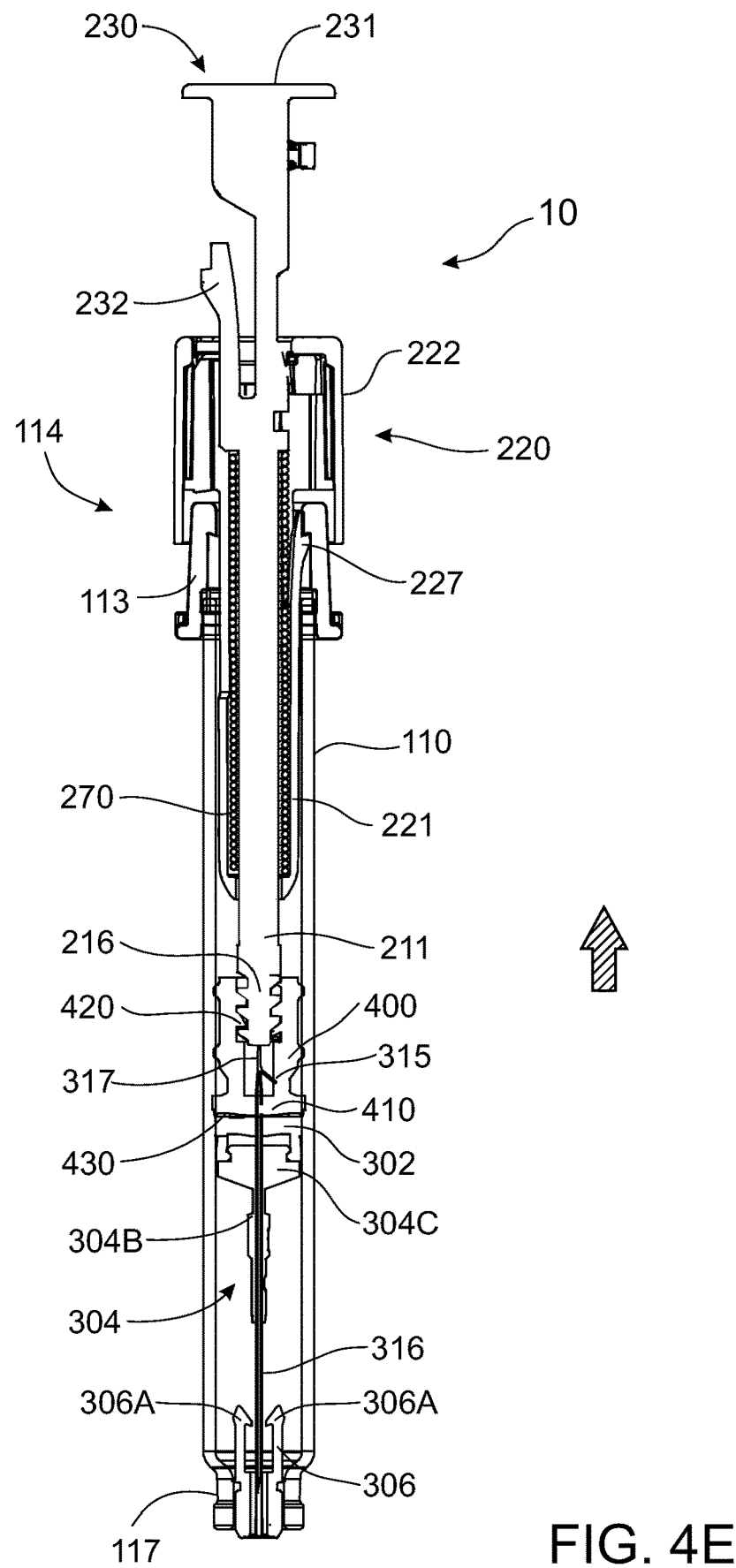
Figure 5E:
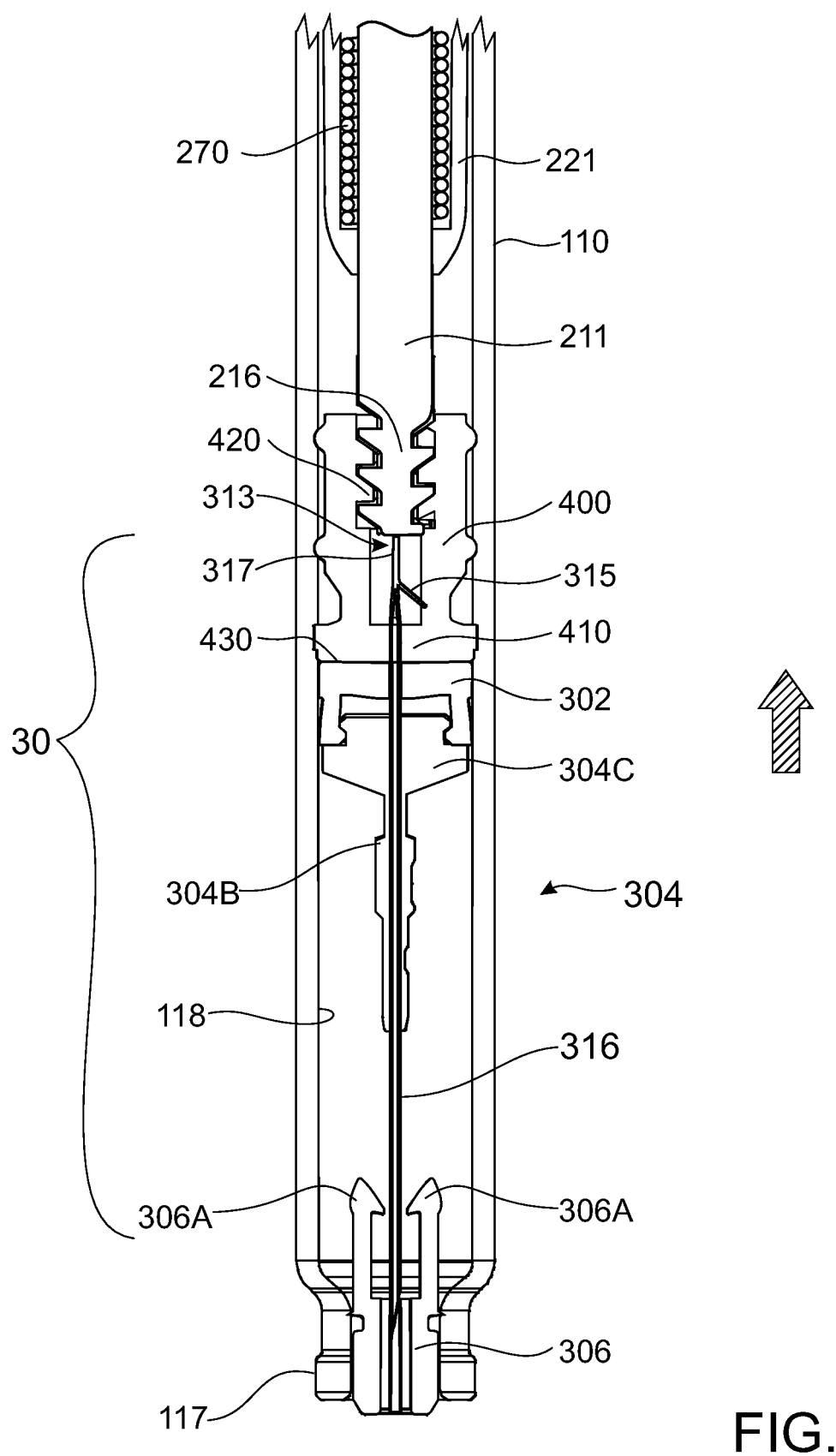
Figure 7:
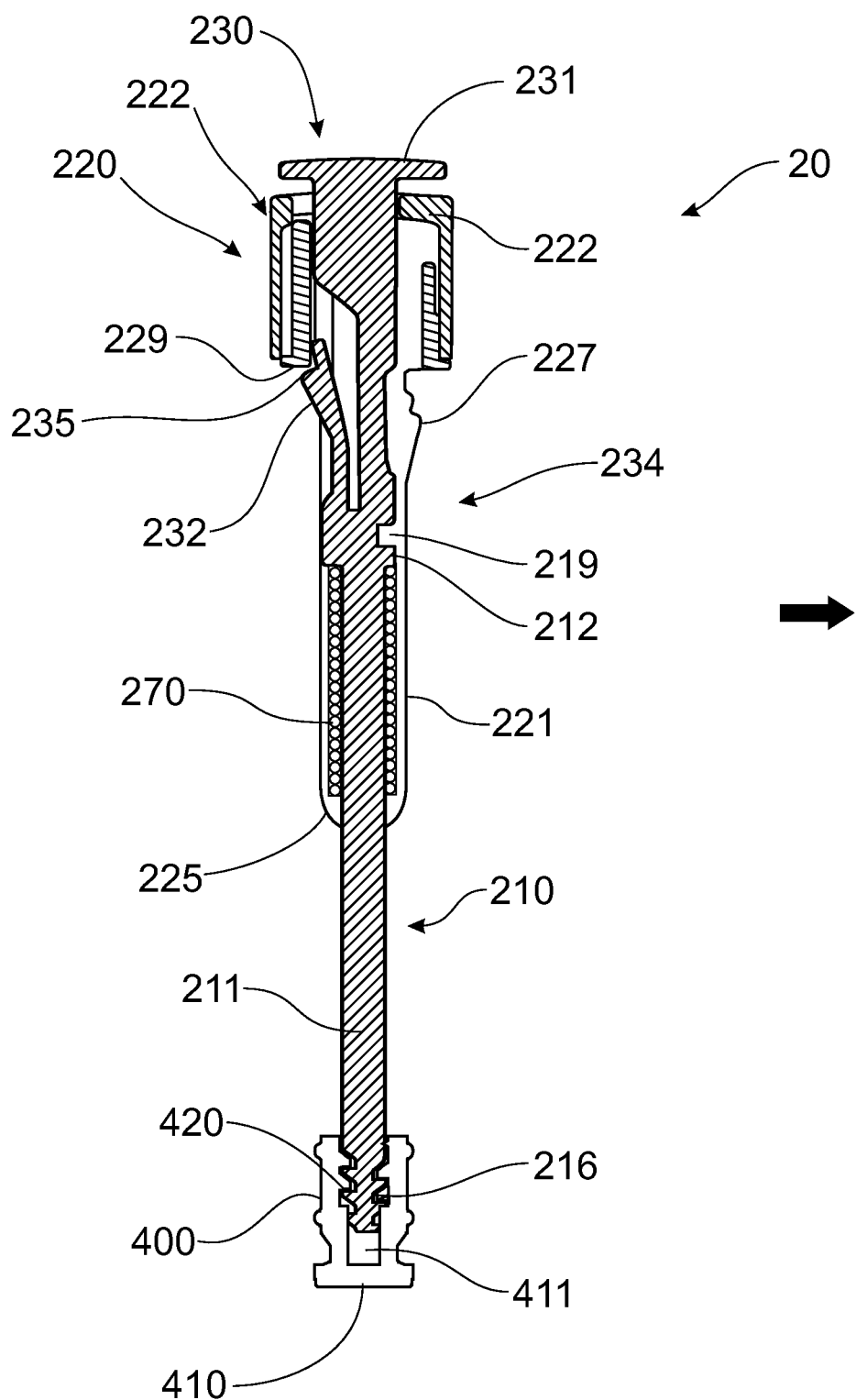
FIG. 7 shows a cross-sectional view of a plunger assembly according to at least one embodiment of the present invention.
Figure 8:
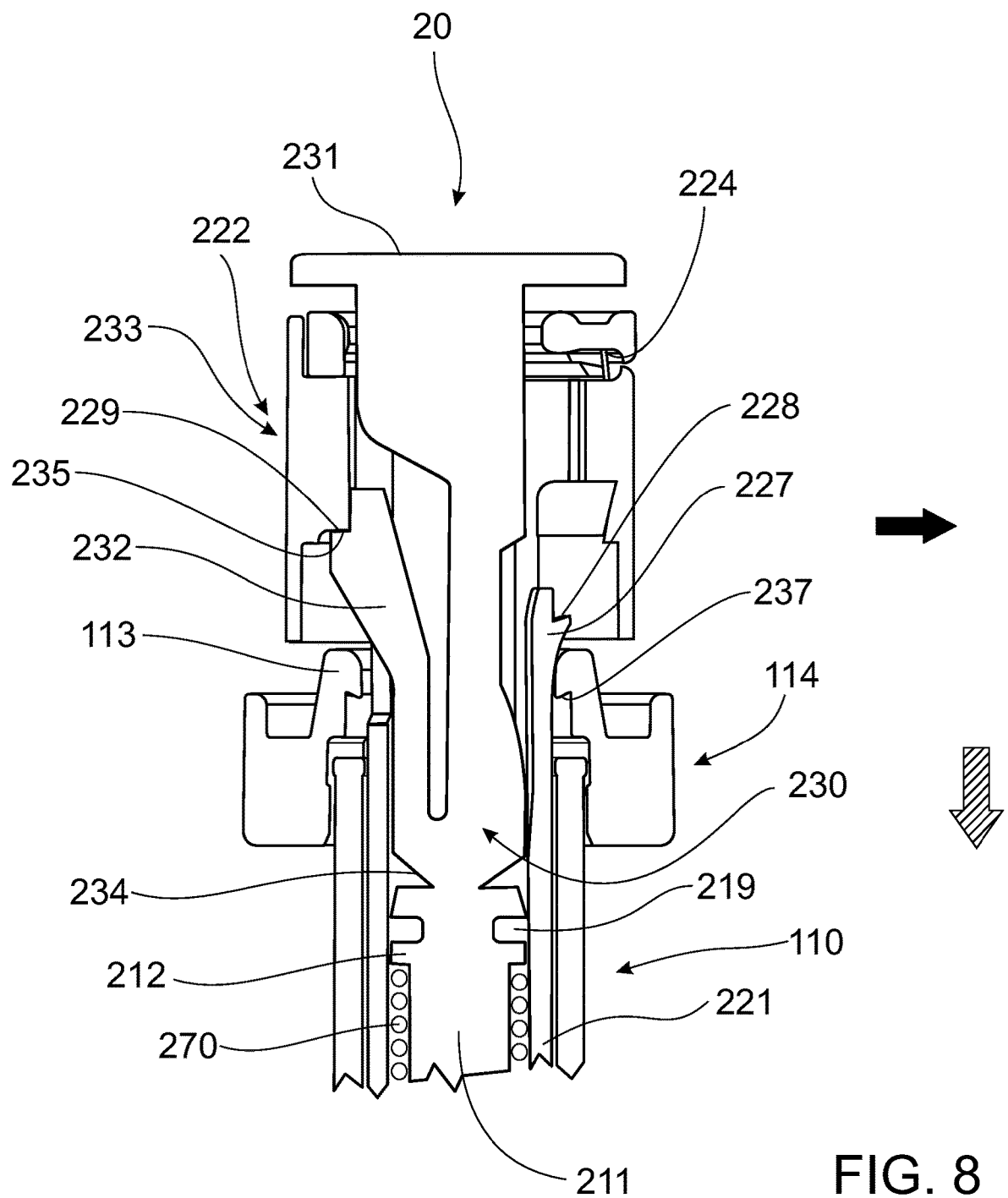
FIG. 8 shows a cross-sectional view of the plunger assembly shown in FIG. 7 just prior to retraction activation.
Figure 9:
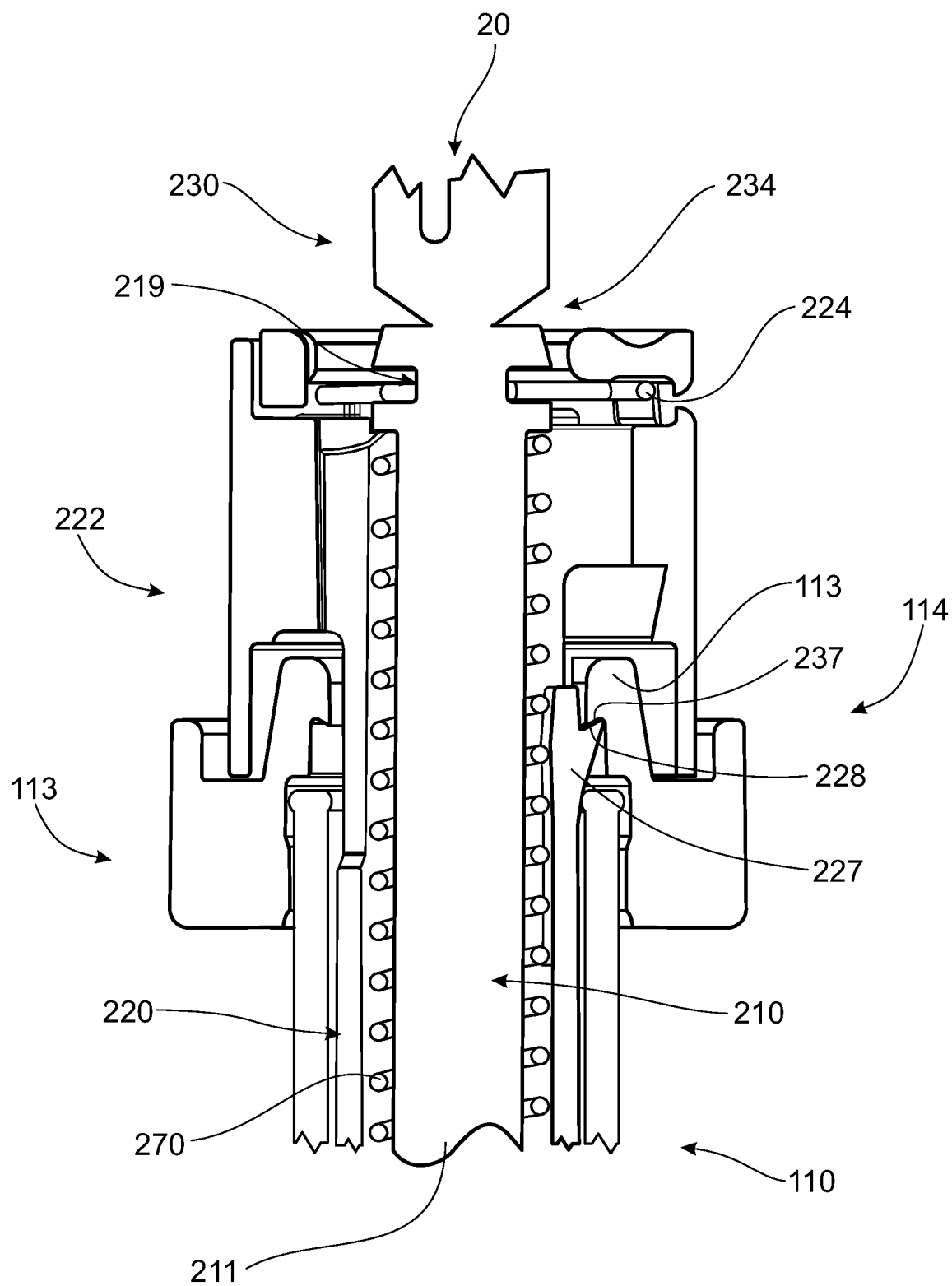
FIG. 9 shows a cross-sectional view of the plunger assembly shown in FIG. 7 after retraction activation.

At the end of needle retraction, as shown in FIGS. 4E and 5E, the retractable needle 310 and/or the entire needle assembly 30 is contained substantially within the barrel 110 to prevent, for example, needle stick injuries. As described above, the rate of needle retraction can be controlled by the user as they reduce the force applied to the plunger assembly 20 upon activation of the needle retraction mechanism. Suitably, syringe 10 comprises one or more locking systems for plunger assembly 20. As shown in FIG. 7-9, in one embodiment of said locking system, plunger outer 220 of plunger assembly 20 comprises locking member 227 which comprises edge 228 engaging underside 237 of release ring 113 after needle retraction to thereby prevent or impede further movement of plunger assembly 20 relative to the release ring, as shown in FIG. 9. Accordingly, in addition to initially assisting in the activation of needle retraction, the release ring 113 may secondarily function to lock delivery plunger 200 after initial use to thereby prevent re-use. Another of said one or more locking systems for plunger assembly 20 is also shown in FIG. 9. After retraction, clip 224 of plunger outer 220 and locking groove 219 of plunger inner 210 co-operate to form a locking system that locks plunger inner 210 and plunger outer 220 together and prevent movement of plunger inner 210 relative to plunger outer 220. At the end of retraction of plunger inner 210 and retractable needle 310, control rod 230 can optionally be broken from plunger inner 210 at optional frangible junction 234 and manually removed from retractable syringe 10 and discarded as "clean" waste so that there is little if any plunger inner 210 protruding externally from the syringe with which to attempt to force delivery plunger assembly 20 back into barrel 110 and attempt to re-engage the needle (not shown). This optional frangible junction 234 (shown in FIG. 9) may be located along plunger inner 210 at a point that would extend in the proximal direction beyond head 222 when the syringe is in the retracted position and, optionally, locked from re-use.

The embodiments of the present invention also provide configurations which allow the use of standard, commercially-available components, thereby reducing overall manufacturing costs, streamlining assembly processes, and avoiding regulatory concerns often associated with non-standard materials and components. For example, the barrel may be made of certain plastics, glass, or any other material commonly used for medical grade products. One or more components of the present invention may also be made up of certain plastics, such as the polycarbonate plastics sold under the trade name "LEXAN" by SABIC Innovative Plastics of Pittsfield, Mass. Similarly, certain elastomeric polymers or rubbers may be utilized, such as the rubber products sold under the trade name "HELVOET" by Datwyler Pharma Packaging USA Inc. of Pennsauken, N.J., for components such as the needle seal 302 and the plunger seal 400. Various medical grade metals, such as stainless steel, may be utilized for the retractable needle 310, as would be appreciated by an ordinarily skilled artisan. These components, the needle assemblies 30, and the safety syringes 10 may be shaped or sized in a myriad of different configurations to meet the desired parameters. These components, needle assemblies 30, and syringes 10 may be assembled, and/or filled with a drug, by a multitude of processes known in the art. For example, well known glues or welding methods such as ultrasonic welding may be employed to assemble the components of the present invention.

Figure 6:
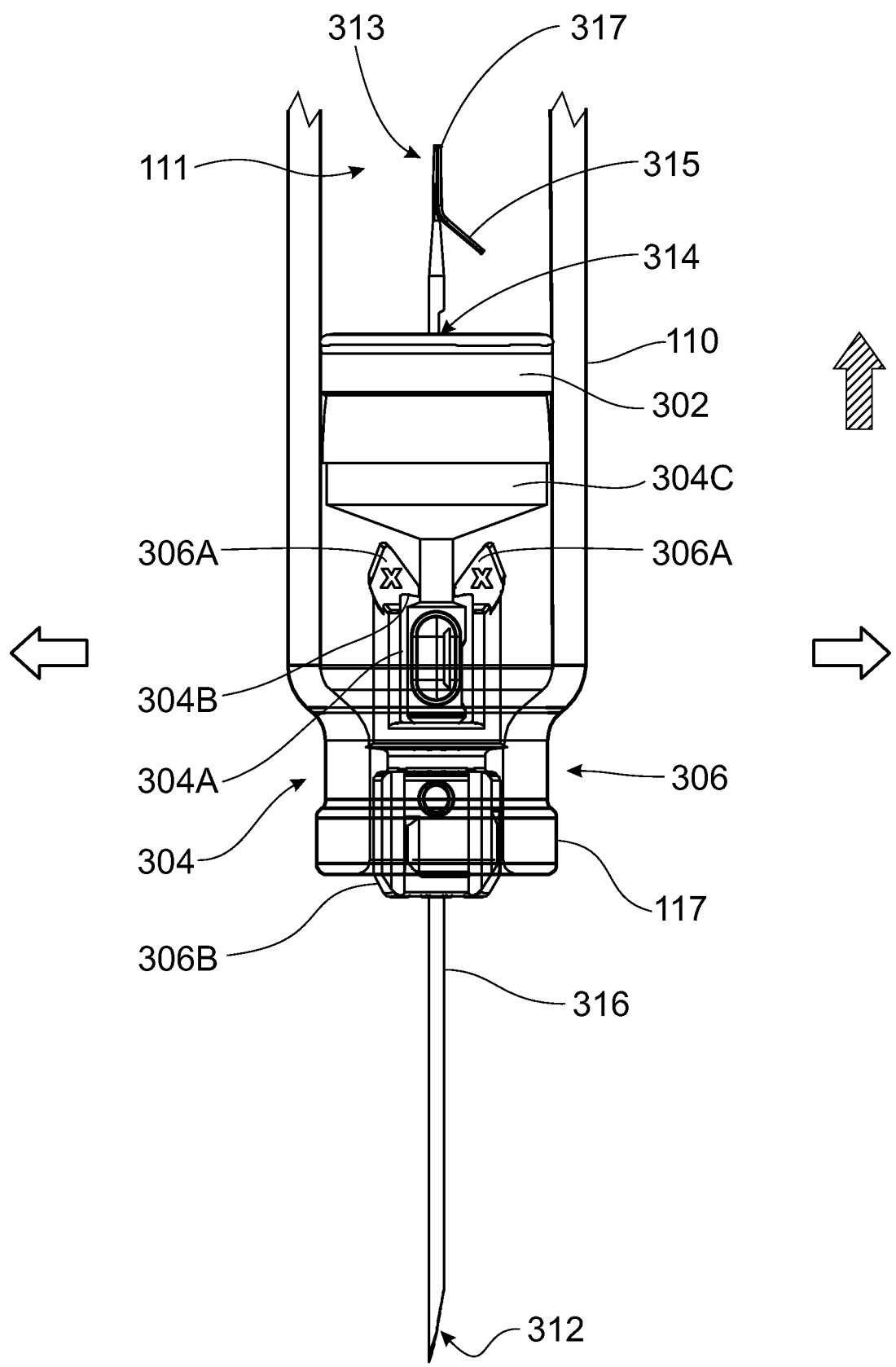
FIG. 6 shows an enlarged assembled view of the needle assembly component shown in FIGS. 5A-5B just prior to needle capture and retraction activation.

The novel needle assembly and syringe designs of the present invention enable relatively simplified assembly and filling processes. One method for assembling a safety syringe having a needle assembly 30, a plunger assembly 20, and a barrel 110 having a longitudinal axis includes the steps of: assembling the needle assembly 30; mounting the needle retainer 306 of the needle assembly 30 to a distal end of the barrel 110; and mounting the plunger assembly 20 to a proximal end of the barrel 110. The needle assembly 30 may be assembled as shown in FIGS. 5A and 5B, which include an optional NOM 304. The final assembly of the needle assembly 30 may be as shown in FIG. 6. The needle assembly 30 may be fixedly mounted, such as by glue, to the distal end of the barrel 110. The plunger assembly 20 may be movably mounted to the distal end of the barrel 110 by first inserting the plunger seal 400 into the barrel 110 and then inserting the plunger rod 211 into the plunger seal 400 by screw connection or another known method of connection. The method for assembling the safety syringe may further include the step of filling the barrel 110 with a drug, after the step of mounting the needle retainer 306 of the needle assembly 30 but prior to the step of mounting the plunger assembly 20.

The plunger seal 400 may comprise of an elastomeric material and be sized such that it provides a compression fit with an inner diameter of the barrel 110 in order to maintain the sterility and container integrity of the internal chamber 411. The plunger seal 400 may also include an aperture, such as an axial pass-through, for example to enable removal of air from the drug chamber as the plunger seal 400 is depressed into position within the barrel 110. Accordingly, the drug may be filled into the barrel 110 prior to mounting of the plunger assembly 20, or just prior to mounting of the plunger seal 400. In the latter configuration, the plunger seal 400 may be slide into position in contact with the drug fluid in a sterile environment or other aseptic conditions. The plunger seal 400 aperture allows for residual air bubbles, if any, to escape the drug chamber when the plunger seal 400 is pushed into contact with the fluid. Subsequently, the plunger seal aperture may be closed or capped by connection with the plunger rod 211, which may be screwed into the plunger seal aperture. The syringe, which may be considered a prefilled syringe, is then ready for use. Alternatively, the components of the present invention may be assembled without the drug filling step, such as in a fill at time-of-use process. In one such process, the drug may be filled by backwards drawing the plunger rod 211 and plunger seal 400 while the needle 310 is aseptically connected to a drug vial. In this manner, the drug fluid is pulled by vacuum action into the drug chamber 111 through the needle 310.

The needle assemblies and safety syringes described herein are configured such that they may readily be manufactured individually, or in a group, as is the case in a tray-based manufacturing and filling process. The safety syringes of the present invention are configured to be used in a manner similar to conventional syringes. The method of use includes the steps: depressing the plunger assembly to facilitate delivery of a drug from the barrel 110; upon completion of the drug delivery, triggering the retraction mechanism to release the biasing member from its energized state; and, by contact between the needle engaging portion 410 of plunger seal 400 and the needle barb 315A of needle 310, causing the needle 310 and/or the needle assembly 30 to retract into the barrel 110.

Regardless of the particular components, the methods of use for the safety syringes of the present invention are relatively similar. By capturing the needle 310 prior to or simultaneously with activation of the retraction mechanism of the plunger assembly 20, the biasing member 270 is allowed to expand causing the needle assembly 30 and/or needle 310 to retract in the proximal direction substantially along a longitudinal axis of the barrel 110. In some embodiments of the present invention, the entire needle assembly 30 is caused to retract, while in other embodiments only certain components thereof, including the needle 310, are caused to retract upon expansion of the biasing member 270. Optionally, the method of use may include the step of blocking, with a clip or lock, the retractable needle 310 from axially translating in the distal direction after the retractable needle 310 has retracted into the barrel 110.

The present invention provides component assemblies, such as needle assemblies, which provide needle retraction, syringes which integrate such safety mechanisms, methods of manufacturing such adapters and safety syringes, and their methods of use. As stated above, the needle assemblies and safety syringes may be utilized in a number of different configurations. For example, as stated above, the novel needle assemblies of the present invention are configured to mate with, be mounted in, or otherwise connect to a barrel, however it may be desirable to pre-form any of the components of the needle assembly to the barrel. Such modifications are contemplated by and encompassed in the embodiments of the present invention. Similarly, the needle assembly may contain a needle-over-mold (NOM) and needle seal, which may be separate components or a dual-purpose single component. Other components may similarly be single components, unified components, or multi-purpose components, as described in the embodiments discussed above. Furthermore, there are a number of different configurations which may utilize the novel needle retraction mechanisms described herein, which may generally be contained substantially within the barrel tip and the distal end of the barrel. Accordingly, similar to the examples provided above, the needle assemblies and safety syringes of the present invention may be configured, modified, and utilized to initiate drug delivery and activate needle retraction in any number of configurations while remaining within the breadth and scope of the present invention. Thus, it is intended that the present invention covers the modifications and variations of this invention provided they come within the scope of the appended claims and their equivalents.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise-indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A retractable syringe comprising:
 a barrel;
 a plunger; and
 a retractable needle assembly comprising:
  a needle retainer comprising at least one flexible arm;
  a needle seal; and
  a cannula that defines a hollow core, the cannula engaged with the needle seal and comprising:
   a delivery tip comprising at least one delivery aperture,
   a proximal end comprising at least one inlet aperture to the hollow core, the inlet aperture in fluid communication with the at least one delivery aperture, and
   at least one projection distal to a proximal tip of the proximal end of the cannula and engageable by the plunger,
   the at least one inlet aperture of the proximal end of the cannula being located distally of the at least one projection and proximally and substantially adjacent to the needle seal,
   the at least one flexible arm of the needle retainer configured to releasably engage the cannula, the needle seal disposed proximally of the needle retainer and configured to seal against an inner wall of the barrel, the needle retainer retaining the cannula such that the cannula and the needle seal remain in a substantially fixed position within the barrel during distal translation of the plunger,
   the plunger configured to push fluid distally toward the inlet aperture and to contact the needle seal at an end of the distal translation, and the at least one flexible arm of the needle retainer configured to flexibly disengage from the cannula to permit retraction of the cannula.

2. The retractable syringe of claim 1, wherein the at least one projection is a barb engageable by the plunger.

3. The retractable syringe of claim 1, wherein the at least one projection is a barb engageable by a plunger seal mounted to the plunger.

4. The retractable syringe of claim 3, wherein the proximal end of the cannula comprises a portion capable of puncturing the plunger seal so that the at least one barb is subsequently engaged by the plunger seal.

5. The retractable syringe of claim 4, wherein the at least one projection is located between the portion capable of puncturing the plunger seal and the at least one inlet aperture.

6. The retractable syringe of claim 1, arranged so that when the at least one projection of the retractable needle is engaged by the plunger before retraction, the at least one inlet aperture is located distal to the plunger or plunger seal.

7. The retractable syringe of claim 1, wherein the plunger comprises a plunger seal that comprises a needle-engaging portion.

8. The retractable syringe of claim 7, wherein the needle-engaging portion is puncturable by the proximal end of the retractable needle to facilitate engagement of the retractable needle.

9. The retractable syringe of claim 1, wherein the plunger seal comprises a substantially flat or planar distal face.

10. The retractable syringe of claim 1, wherein the plunger comprises a plunger outer, a plunger rod and a biasing member, wherein the plunger outer and plunger rod so-operate to maintain the biasing member in an initially energized state.

11. The retractable syringe of claim 10, wherein disengagement of the plunger outer and the plunger rod facilitate release of the biasing member to thereby retract the retractable needle when engaged with the plunger.

12. The retractable syringe of claim 1, wherein the needle seal is an elastomeric seal.

13. The retractable syringe of claim 1, further comprising a needle-over-mold fixedly attached to the cannula, the needle retainer configured to releasably engage the needle-over-mold.

* * * * *